(12) United States Patent
Mor et al.

(10) Patent No.: US 12,290,145 B2
(45) Date of Patent: May 6, 2025

(54) MODULAR FOOTWEAR PROTUBERANCE ASSEMBLY

(71) Applicant: APOS MEDICAL ASSETS LTD., Tel Aviv (IL)

(72) Inventors: Amit Mor, Rehovot (IL); Avi Elbaz, Dimona (IL); Oren Livne, Tel Aviv (IL)

(73) Assignee: APOS MEDICAL ASSETS LTD., Tel Aviv (IL)

( * ) Notice: Subject to any disclaimer, the term of this patent is extended or adjusted under 35 U.S.C. 154(b) by 0 days.

(21) Appl. No.: 18/732,867

(22) Filed: Jun. 4, 2024

(65) Prior Publication Data

US 2024/0315389 A1 Sep. 26, 2024

Related U.S. Application Data

(63) Continuation of application No. 17/734,474, filed on May 2, 2022, now Pat. No. 12,029,278, which is a (Continued)

(51) Int. Cl.
*A43B 7/1405* (2022.01)
*A43B 7/144* (2022.01)
(Continued)

(52) U.S. Cl.
CPC .............. *A43B 7/141* (2013.01); *A43B 7/144* (2013.01); *A43B 7/1445* (2013.01); *A43B 7/24* (2013.01);
(Continued)

(58) Field of Classification Search
CPC ........... A43B 7/141; A43B 7/24; A43B 21/37; A43B 21/433; A43B 21/48; A43B 21/50; A43B 21/51; A61F 5/0127; A61H 1/0266
See application file for complete search history.

(56) References Cited

U.S. PATENT DOCUMENTS 3,063,169 A 11/1962 Cortina
3,481,332 A 12/1969 Arnold
(Continued)

FOREIGN PATENT DOCUMENTS

CN 101279636 A 10/2008
DE 1907894 1/1965
(Continued)

OTHER PUBLICATIONS

Apos Therapy. Apos Therapy—How it works. Youtube [online] [video]. Nov. 20, 2013. Retrieved from <https://www.youtube.com/watch?v=mjqloxr9bYU>.
(Continued)

*Primary Examiner* — Ted Kavanaugh
(74) *Attorney, Agent, or Firm* — The Roy Gross Law Firm, LLC; Roy D. Gross

(57) ABSTRACT

A footwear device comprising: a sole assembly comprising at least one connective element; at least one protuberance assembly comprising a base and a cap, said base and cap configured to rotatively align; a locking fixture configured to lock and unlock said alignment of said base and cap; and a fastening fixture configured to fasten said base to said track in a selected position in said track.

3 Claims, 28 Drawing Sheets

Related U.S. Application Data continuation of application No. 16/994,621, filed on Aug. 16, 2020, now Pat. No. 11,363,852, which is a continuation of application No. 15/735,360, filed as application No. PCT/IL2016/050610 on Jun. 9, 2016, now Pat. No. 10,750,812.

(60) Provisional application No. 62/174,111, filed on Jun. 11, 2015.

(51) Int. Cl.
| | | |
|---|---|---|
| *A43B 7/1445* | (2022.01) | |
| *A43B 7/24* | (2006.01) | |
| *A43B 13/14* | (2006.01) | |
| *A61B 5/11* | (2006.01) | |
| *A61F 5/01* | (2006.01) | |
| *A61H 1/02* | (2006.01) | |
| *A61H 3/00* | (2006.01) | |
| *A61H 23/02* | (2006.01) | |

(52) U.S. Cl.
CPC ............ *A43B 13/145* (2013.01); *A61B 5/112* (2013.01); *A61F 5/0127* (2013.01); *A61H 1/0266* (2013.01); *A61H 3/00* (2013.01); *A61H 23/02* (2013.01); *A61H 1/024* (2013.01); *A61H 2201/164* (2013.01); *A61H 2201/165* (2013.01); *A61H 2205/12* (2013.01)

(56) References Cited

U.S. PATENT DOCUMENTS

| | | |
|---|---|---|
| 3,668,792 A | 6/1972 | York |
| 3,797,136 A | 3/1974 | Soleri |
| 4,670,996 A | 6/1987 | Dill |
| 4,805,320 A | 2/1989 | Goldenberg et al. |
| 4,907,355 A | 3/1990 | Allen et al. |
| 5,251,508 A | 10/1993 | Robbins |
| 5,524,365 A | 6/1996 | Goldenberg |
| 6,035,559 A | 3/2000 | Freed et al. |
| 6,108,944 A | 8/2000 | Savoie |
| 6,494,117 B1 | 12/2002 | Bryne |
| 6,979,287 B2 | 12/2005 | Elbaz et al. |
| 7,101,330 B2 | 9/2006 | Elbaz et al. |
| 7,462,158 B2 | 12/2008 | Mor |
| 8,453,354 B2 | 6/2013 | Baker |
| 8,533,980 B2 | 9/2013 | Elbaz et al. |
| 8,713,817 B2 | 5/2014 | Litchfield et al. |
| 8,758,207 B2 | 6/2014 | Elbaz et al. |
| 9,055,788 B2 | 6/2015 | Elbaz et al. |
| 9,271,895 B2 | 3/2016 | Mor et al. |
| 9,357,812 B2 | 6/2016 | Elbaz et al. |
| 10,182,609 B2 | 1/2019 | Bryne |
| 10,750,812 B2 | 8/2020 | Mor |
| 11,363,852 B2 * | 6/2022 | Mor .......................... A43B 5/14 |
| 12,029,278 B2 * | 7/2024 | Mor .......................... A61H 3/00 |
| 2004/0079001 A1 | 4/2004 | McMullin |
| 2006/0021260 A1 | 2/2006 | Kim |
| 2007/0209239 A1 | 9/2007 | Kelly |
| 2007/0271816 A1 | 11/2007 | Workman et al. |
| 2010/0186262 A1 | 7/2010 | Krikorian et al. |
| 2011/0047831 A1 | 3/2011 | Elbaz et al. |
| 2011/0126422 A1 | 6/2011 | Vattes et al. |
| 2013/0196829 A1 | 8/2013 | Elbaz et al. |
| 2015/0119767 A1 | 4/2015 | Mor et al. |

FOREIGN PATENT DOCUMENTS

| | | |
|---|---|---|
| DE | 29701013 | 3/1997 |
| DE | 29902731 U1 | 3/2000 |
| DE | 10133863 | 2/2003 |
| EP | 0925809 | 6/1999 |
| EP | 1038459 | 9/2000 |
| EP | 2462827 | 6/2012 |
| FR | 1128009 | 1/1957 |
| FR | 2820329 | 8/2002 |
| JP | S61119282 | 1/1986 |
| JP | H114842 A | 1/1999 |
| JP | 2000084035 A | 3/2000 |
| JP | 2005287726 A | 10/2005 |
| JP | 2006247197 B2 | 9/2006 |
| JP | 2007029700 | 2/2007 |
| JP | 2008264023 A | 11/2008 |
| JP | 2009018124 A | 1/2009 |
| JP | 2010115291 B2 | 5/2010 |
| KR | 20030058556 | 7/2003 |
| NL | 8502659 | 4/1987 |
| RU | 2033132 C1 | 4/1995 |
| WO | 1996020651 | 7/1996 |
| WO | 1997013422 | 4/1997 |
| WO | 2000067846 | 11/2000 |
| WO | 2001037693 | 5/2001 |
| WO | 2002037995 | 5/2002 |
| WO | 2003090868 | 11/2003 |
| WO | 2004016321 | 2/2004 |
| WO | 2004043185 | 5/2004 |
| WO | 2006005139 | 1/2006 |
| WO | 2011024162 | 3/2011 |
| WO | 2012001685 | 1/2012 |
| WO | 2013084213 | 6/2013 |

OTHER PUBLICATIONS

International Search Report PCT/IL2016/050610 Completed Sep. 25, 2016; Mailed Sep. 28, 2016 3 pages.

Written Opinion of the International Searching Authority PCT/IL2016/050610 Mailed Sep. 28, 2016 4 pages.

Cerruto M.A., The Effect of Ankle Inclination in Upright Position on the Electromyigraphic Activity of Pelvic Floor . . . , 320, Eur Urol Suppl 2007;6(2):102.

* cited by examiner

901

902

901

904

905

MODULAR FOOTWEAR PROTUBERANCE ASSEMBLY

CROSS REFERENCE TO RELATED APPLICATIONS

This application is a continuation of U.S. patent application Ser. No. 17/734,474 filed May 2, 2022, which is a continuation of U.S. patent application Ser. No. 16/994,621 filed Aug. 16, 2020 (issued as U.S. Pat. No. 11,363,852), which is a continuation of U.S. patent application Ser. No. 15/735,360 filed Dec. 11, 2017 (Issued As U.S. Pat. No. 10,750,812), which is a National Phase of PCT Patent Application No. PCT/IL2016/050610 having International filing date of Jun. 9, 2016, which claims the benefit of priority of U.S. Patent Application No. 62/174,111 filed on Jun. 11, 2015. The contents of the above applications are all incorporated by reference as if fully set forth herein in their entirety.

FIELD OF THE INVENTION

This invention relates to the field of treatment of medical conditions and to AposTherapy, in particular.

BACKGROUND OF THE INVENTION

AposTherapy is a medical program providing a therapeutic effect for the treatment of various medical conditions, specifically, orthopedic conditions. AposTherapy is based on an individually calibrated footwear biomechanical device (or simply "footwear device"). AposTherapy may address the biomechanical abnormalities characteristic of various orthopedic conditions, including the body's mal-alignment, muscle weakness, impaired neuromuscular control and the resulted abnormal pathological movement patterns. Main goals of the treatment include promotion and restoration of desired motor pattern and relief of pain.

The treatment is based on the footwear device which may be individually-calibrated by a physical therapist. The calibration may be based on a particular methodology coupled by computerized gait, pain, function and quality of life measurements (such as Western Ontario and McMaster Universities Arthritis Index (WOMAC) and the Short Form (36) Health Survey (SF-36) questionnaires). The device may combine two rehabilitation principles, bringing the body and chain of joints to an optimal alignment, while simultaneously introducing perturbation through the creation of controlled micro-instability through the patients' entire step-cycle.

First, by adjusting the foot's point of contact with the ground (the center of pressure), the device may re-distributes the loads acting on the various joints of the lower limb. Second, controlled micro-instability may be introduced through perturbation during the gait cycle (and any other weight bearing activity). This may restore neuromuscular control and over time retrains the muscles to adopt an optimal movement pattern.

The device may use two convex-shaped pods (i.e., pods which provide perturbation, also referred herein as 'protuberances') under the main weight bearing areas of the foot, such as the heel and the forefoot. One may adjust their location, height, and resilience. The level of perturbation may be adjusted by varying the convexity of the pods.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

One embodiment provides a footwear device comprising: a sole assembly comprising a connective element; at least one protuberance assembly comprising a base and a cap, said base and cap configured to rotatively align; a locking fixture configured to lock and unlock said alignment of said base and cap; and a fastening fixture configured to fasten said base to said connective element at a selected position in said sole assembly.

Optionally, said connective element is a track, and wherein said fastening fixture comprises: a track nut movably disposed in said track; and a screw configured to be screwed to said nut.

Optionally, said base comprises a screw bore positioned in an eccentric manner with respect to said protuberance assembly, said screw bore configured to allow fastening of said base to said track in said selected position by said screw and said track nut; and said cap comprises a bore positioned correspondingly to said screw bore configured to allow access to said screw through said cap.

Optionally, the footwear device further comprises a footwear, wherein said footwear comprises said sole assembly.

Optionally, said at least one protuberance assembly is two protuberance assemblies.

Optionally, said sole assembly further comprises a securing fixture configured to secure said sole assembly to a footwear.

Another embodiment provides a protuberance assembly comprising: a base comprising: a plurality of peripheral rim portions spaced apart, wherein each of said peripheral rim portions ends with a downwards protruding stopper, and a screw bore configured to allow screwing of said base to a sole assembly, wherein said bore is positioned in an eccentric manner with respect to said protuberance assembly; and a cap comprising: a plurality of internally protruding portions spaced apart, each of said plurality of internally protruding portions corresponding to one of said plurality of peripheral rim portions, and a bore positioned correspondingly to said screw bore of said base, wherein when said cap is placed on said base and rotated, each of said plurality of internally protruding portions arrives under its corresponding peripheral rim portion and stopped by said downward protruding stopper of said corresponding peripheral rim portion, thereby aligning said base and said cap.

Optionally, said base further comprises a socket ending with an opening in a peripheral wall of said base, said socket configured to accommodate a locking fixture, said locking fixture comprising a locking pin and a spring, and wherein said locking fixture is configured to lock said alignment of said base and cap when placed in said socket.

A further embodiment provides a method for adjusting a device comprising a protuberance assembly mounted to a selected position on a bottom surface of a sole, said protuberance assembly comprising a base and a cap, wherein said base and cap are aligned and locked, the method comprising: unlocking the alignment of said base and cap; rotating said cap on said base to remove said cap from said base, wherein said base is kept firmly mounted to said selected position in said bottom surface of said sole; rotating another cap on said base until an alignment of said another cap with said base is achieved; and locking said alignment of said another cap and said base.

Optionally, said base further comprises a socket ending with an opening in a peripheral wall of said base, said socket configured to accommodate a locking fixture, said locking fixture comprising a locking pin and a spring, and wherein said locking fixture is configured to lock said alignment of said base and cap when placed in said socket.

Optionally, the method further comprises calibrating said device by firmly mounting said protuberance assembly to said selected position in said bottom surface of said sole.

Optionally, said sole comprises at least one track and said protuberance assembly comprises a fastening fixture which comprises: a track nut movably disposed in said track; and a screw configured to be screwed in said nut.

Optionally, said base comprises a screw bore positioned in an eccentric manner with respect to said protuberance assembly, said screw bore configured to allow fastening of said base to said track in said selected position by said screw and said track nut, and said cap comprises a bore positioned correspondingly to said screw bore configured to allow access to said screw through said cap.

Yet another embodiment provides a method for manufacturing a footwear device, the method comprising assembling together: a sole assembly which comprises at least one track; at least one protuberance assembly comprising a base and a cap which are configured to rotatively align; a locking fixture configured to lock and unlock said alignment of said base and cap; and producing a fastening fixture configured to fasten said base to said track in a selected position in said track.

Optionally, said connective element is a track, and wherein said fastening fixture comprises: a track nut movably disposed in said track; and a screw configured to be screwed in said nut.

Optionally, said base comprises a screw bore positioned in an eccentric manner with respect to said protuberance assembly, said screw bore configured to allow fastening of said base to said track in said selected position by said screw and said track nut, and said cap comprises a bore positioned correspondingly to said screw bore configured to allow access to said screw through said cap.

Optionally, the method further comprises assembling said footwear device to a footwear.

Optionally, said sole assembly further comprises a securing fixture configured to secure said sole assembly to the footwear.

In addition to the exemplary aspects and embodiments described above, further aspects and embodiments will become apparent by reference to the figures and by study of the following detailed description.

BRIEF DESCRIPTION OF THE DRAWINGS

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION OF THE INVENTION

Figure 1:
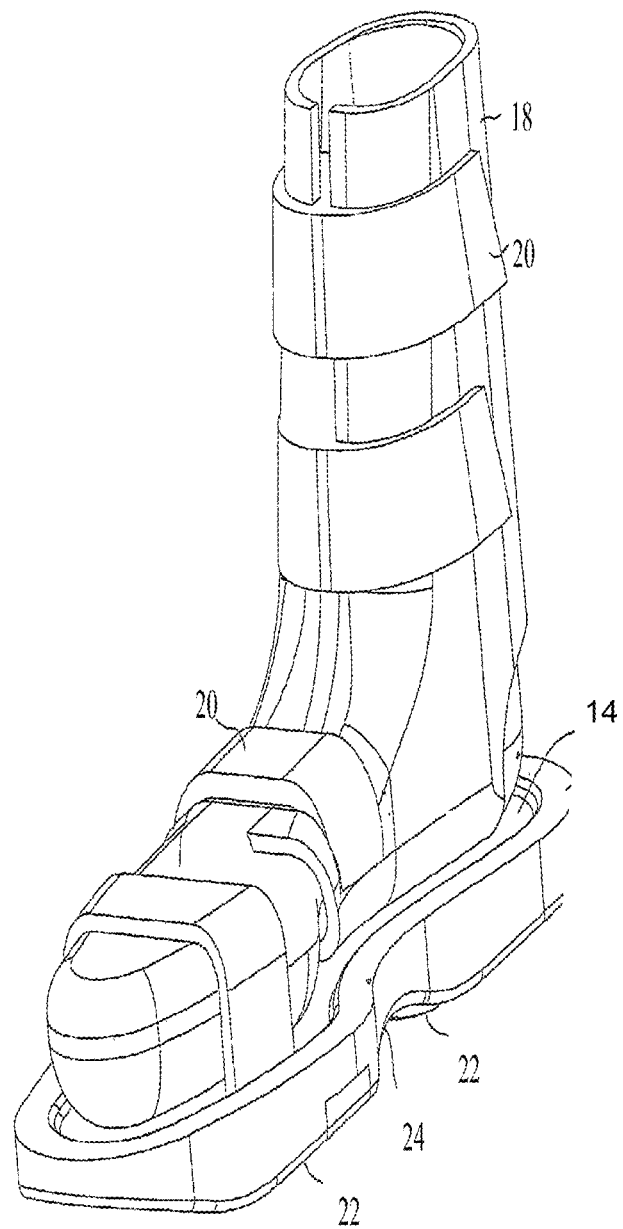
FIG. 1 is a simplified pictorial illustration of footwear constructed and operative in accordance with an embodiment.

The disclosed devices, assemblies and methods may allow the adjustment of a footwear device without the need to recalibrate it. The footwear device may be adjusted by replacing its protuberances. Such an adjustment may be required, for example, in order to replace a worn out or damaged protuberance and/or in order to replace the protuberance with another protuberance, which is different in at least one effective characteristic. The effective characteristic may be, for example, the height, curvature or shape of the protuberance, which may affect the treatment of the patient using the device. Such a replacement may be, for example, due to change in the treatment plan or as part of the treatment plan. When using a single-part protuberance, such a replacement means completely removing the protuberance from the device and repositioning its replacement with respect to the device (i.e., recalibrating the device).

A protuberance assembly is herein disclosed which may include two separate portions: a cap and a base, which may be rotatively aligned and locked (i.e., fixedly attached), or misaligned and unlocked (i.e., detached). Thus, the base may remain fixed to its position in or on the device while the cap may be removed and replaced. Therefore, the complex task of replacing the protuberance and recalibrating the device is simplified to replacing of the cap only. In some embodiments, there is no longer a need for a specialist in order to perform such a task. In other embodiments, a specialist may still be employed to perform the task.

The terms "track" and "rail" and their derivations, may be used herein interchangeably.

The term "adjust" and its derivations as referred to herein, may also refer to the operations of fixing, modifying, changing, replacing and/or renewing.

Methods

There is provided a method for increasing bone density in a subject suffering from diminished bone mass in a lower limb bone such as the femur. The method may include a first step of securing a footwear device (or simply "the device" or "the footwear") to a subject's foot, whereby the device may include a foot securing mean, a support member operably attached to the securing mean, and a moveable anterior bulbous protuberance (BP) and a moveable bulbous posterior protuberance. The method may include a second step of calibrating the posterior protuberance and the anterior protuberance to a balanced position, wherein the balanced position may include a position whereby the device provides a reduced inversion or a reduced eversion to the subject's foot during the stance phases. The method may include a third step of fixing the posterior protuberance and the anterior protuberance to the support member in the balanced position. In some embodiments, diminished bone mass in a lower limb bone such as the femur according to disclosed method may cause a defective gait or a gait disorder. In some embodiments, diminished bone mass is diminished bone density. In some embodiments, diminished bone mass is diminished bone mineral density.

In some embodiments, a method for treating a subject afflicted with osteoporosis or osteopenia is provided. The method may include a first step of securing a footwear device (or simply "the device") to a subject's foot, whereby the device may include a foot securing mean, a support member operably attached to the securing mean, and a moveable anterior bulbous protuberance and a moveable bulbous posterior protuberance. The method may include a second step of calibrating the posterior protuberance and the anterior protuberance to a balanced position, wherein the balanced position may include a position whereby the device provides a reduced inversion or a reduced eversion to the subject's foot during the stance phases. The method may include a third step of fixing the posterior protuberance and the anterior protuberance to the support member in the balanced position.

In some embodiments, a method for reducing the risk of osteoporosis in a subject at risk of acquiring osteoporosis may be provided. The method may include a first step of securing a footwear device (or simply "the device") to a subject's foot, whereby the device may include a foot securing mean, a support member operably attached to the securing mean, and a moveable anterior protuberance and a moveable posterior protuberance. The method may include a second step of calibrating the posterior protuberance and the anterior protuberance to a balanced position. The balanced position may include a position whereby the device may provide a reduced inversion or a reduced eversion to the subject's foot during the stance phases. The method may include a third step of fixing the posterior protuberance and the anterior protuberance to the support member in the balanced position, thereby, reducing the risk of osteoporosis in a subject at risk of acquiring osteoporosis.

In some embodiments, a subject at risk of acquiring osteoporosis suffers from lack of estrogen (women) or androgen (men). In some embodiments, a subject at risk of acquiring osteoporosis is a lady older than 60 years of age. In some embodiments, a subject at risk of acquiring osteoporosis is a menopausal lady. In some embodiments, a subject at risk of acquiring osteoporosis suffers from inadequate intake of calcium. In some embodiments, a subject at risk of acquiring osteoporosis suffers from inadequate intake of vitamin D. In some embodiments, a subject at risk of acquiring osteoporosis suffers from lack of weight-bearing exercise. In some embodiments, a subject at risk of acquiring osteoporosis suffers from age-related changes in endocrine functions. In some embodiments, a subject at risk of acquiring osteoporosis overuses corticosteroids (Cushing syndrome).

In some embodiments, a subject at risk of acquiring osteoporosis suffers from a thyroid deficiency. In some embodiments, a subject at risk of acquiring osteoporosis is not engaged in physical activity (lack of muscle use). In some embodiments, a subject at risk of acquiring osteoporosis suffers or suffered from bone cancer. In some embodiments, a subject at risk of acquiring osteoporosis consumes low calcium diet. In some embodiments, a subject at risk of acquiring osteoporosis is a thin woman of advanced age. In some embodiments, a subject at risk of acquiring osteoporosis has a family member with osteoporosis. In some embodiments, a woman at risk of acquiring osteoporosis went through surgically induced menopause, or abnormal or absence of menstrual periods. In some embodiments, a subject at risk of acquiring osteoporosis suffers from an eating disorder such as anorexia nervosa or bulimia. In some embodiments, a subject at risk of acquiring osteoporosis suffers from alcoholism. In some embodiments, a subject at risk of acquiring osteoporosis suffers from inactive lifestyle. In some embodiments, a subject at risk of acquiring osteoporosis consumes corticosteroids and/or anticonvulsants. In some embodiments, a subject at risk of acquiring osteoporosis suffers from rheumatoid arthritis.

In some embodiments, a subject at risk of acquiring osteoporosis suffers from Turner syndrome. In some embodiments, a subject at risk of acquiring osteoporosis suffers from Klinefelter syndrome. In some embodiments, a subject at risk of acquiring osteoporosis suffers from Kallmann syndrome. In some embodiments, a subject at risk of acquiring osteoporosis suffers from andropause. In some embodiments, a subject at risk of acquiring osteoporosis suffers from hypothalamic amenorrhea. In some embodiments, a subject at risk of acquiring osteoporosis suffers from hyperprolactinemia. In some embodiments, a subject at risk of acquiring osteoporosis suffers from Cushing's syndrome. In some embodiments, a subject at risk of acquiring osteoporosis suffers from hyperparathyroidism. In some embodiments, a subject at risk of acquiring osteoporosis suffers from thyrotoxicosis. In some embodiments, a subject at risk of acquiring osteoporosis suffers from hypothyroidism. In some embodiments, a subject at risk of acquiring osteoporosis suffers from diabetes mellitus type 1 or 2. In some embodiments, a subject at risk of acquiring osteoporosis suffers from acromegaly. In some embodiments, a subject at risk of acquiring osteoporosis suffers from adrenal insufficiency.

In some embodiments, a subject at risk of acquiring osteoporosis suffers from malnutrition. In some embodiments, a subject at risk of acquiring osteoporosis suffers from malabsorption. In some embodiments, a subject at risk of acquiring osteoporosis suffers from coeliac disease. In some embodiments, a subject at risk of acquiring osteoporosis suffers from Crohn's disease. In some embodiments, a subject at risk of acquiring osteoporosis suffers from lactose intolerance In some embodiments, a subject at risk of acquiring osteoporosis suffers from severe liver disease (especially primary biliary cirrhosis). In some embodiments, a subject at risk of acquiring osteoporosis suffers from bulimia. In some embodiments, a subject at risk of acquiring osteoporosis suffers from vitamin K or vitamin B12 deficiency.

In some embodiments, a subject at risk of acquiring osteoporosis suffers from ankylosing spondylitis. In some embodiments, a subject at risk of acquiring osteoporosis suffers from systemic lupus erythematosus. In some embodiments, a subject at risk of acquiring osteoporosis suffers from polyarticular juvenile idiopathic arthritis. In some embodiments, a subject at risk of acquiring osteoporosis suffers from myeloma. In some embodiments, a subject at risk of acquiring osteoporosis suffers from a monoclonal gammopathies. In some embodiments, a subject at risk of acquiring osteoporosis suffers from lymphoma. In some embodiments, a subject at risk of acquiring osteoporosis suffers from leukemia. In some embodiments, a subject at risk of acquiring osteoporosis suffers from mastocytosis. In some embodiments, a subject at risk of acquiring osteoporosis suffers from hemophilia. In some embodiments, a subject at risk of acquiring osteoporosis suffers from sickle-cell disease. In some embodiments, a subject at risk of acquiring osteoporosis suffers from thalassemia.

In some embodiments, a subject at risk of acquiring osteoporosis suffers from osteogenesis imperfect. In some embodiments, a subject at risk of acquiring osteoporosis suffers from Marfan syndrome. In some embodiments, a subject at risk of acquiring osteoporosis suffers from hemochromatosis. In some embodiments, a subject at risk of acquiring osteoporosis suffers from hypophosphatasia. In some embodiments, a subject at risk of acquiring osteoporosis suffers from a glycogen storage disease. In some embodiments, a subject at risk of acquiring osteoporosis suffers from homocystinuria. In some embodiments, a subject at risk of acquiring osteoporosis suffers from Ehlers-Danlos syndrome. In some embodiments, a subject at risk of acquiring osteoporosis suffers from porphyria. In some embodiments, a subject at risk of acquiring osteoporosis suffers from Menkes' syndrome. In some embodiments, a subject at risk of acquiring osteoporosis suffers from epidermolysis bullosa. In some embodiments, a subject at risk of acquiring osteoporosis suffers from Gaucher's disease. In some embodiments, a subject at risk of acquiring osteoporosis suffers from scoliosis. In some embodiments, a subject at risk of acquiring osteoporosis suffers from complex regional pain syndrome. In some embodiments, a subject at risk of acquiring osteoporosis suffers from Parkinson's disease. In some embodiments, a subject at risk of acquiring osteoporosis suffers from chronic obstructive pulmonary disease.

In some embodiments, a subject treatable by the disclosed methods can walk. In some embodiments, a subject treatable by the disclosed methods can walk with prosthesis. In some embodiments, a subject treatable by the disclosed methods can walk with leg prosthesis. In some embodiments, a subject treatable by the disclosed methods can walk and has feet or feet like prosthesis to accommodate the device (footwear).

In some embodiments, treating is reducing the risk of fractures. In some embodiments, treating is reducing the risk of fractures in bones in the lower limb. In some embodiments, treating is reducing the risk of a compression fracture. In some embodiments, treating is reducing the risk of vertebral fractures. In some embodiments, treating is reversing diminished bone density. In some embodiments, treating is increasing bone density. In some embodiments, treating is increasing bone mass. In some embodiments, treating is reversing osteoporosis. In some embodiments, treating is improving gait. In some embodiments, treating is improving gait and increasing bone density. In some embodiments, treating is reversing osteopenia. In some embodiments, the pathologies and syndromes described herein cause enormous pain and even death. In some embodiments, the methods as described herein reduce the risk associated with enormous pain. In some embodiments, treating is treating a subject afflicted with osteopenia. In some embodiments, treating is treating a subject afflicted with osteoporosis.

In some embodiments, the disclosed methods may inhibit bone resorption. In some embodiments, the disclosed methods may induce bone formation. In some embodiments, the disclosed methods may inhibit bone resorption and may induce bone formation. In some embodiments, the disclosed methods may balance the ratio of trabecular bone to cortical bone ratio.

In some embodiments, the disclosed methods may maintain bone mineral density (BMD) in a subject suffering from a decline in BMD. In some embodiments, the disclosed methods may increase BMD in a subject suffering from a decline in BMD. In some embodiments, the subject is a postmenopausal woman. In some embodiments, the disclosed methods may increase BMD and moment of inertia of the proximal tibia in a subject in need thereof such as a subject suffering from osteoporosis. In some embodiments, the disclosed methods may increase of L2-L4 BMD in osteopenic patients such as postmenopausal women. In some embodiments, the disclosed methods may elicit improvements in distal radius and hip BMD. In some embodiments, the disclosed methods may increase BMD improve balance, gait, reduce the risk of falls or any combination thereof.

In some embodiments, diminished bone mass in a lower limb is osteoporosis. In some embodiments, diminished bone mass in a lower limb is coupled to increased risk of fracture. In some embodiments, diminished bone mass is diminished bone mineral density (BMD). In some embodiments, diminished bone mass in a lower limb is coupled to abnormal bone microarchitecture.

In some embodiments, diminished bone mass in a lower limb is a bone mineral density that is 1.8 standard deviations or more below the mean peak bone mass (average of young and healthy adults) as measured by Dual-energy X-ray Absorptiometric (DXA). In some embodiments, diminished bone mass in a lower limb is a bone mineral density that is 2.0 standard deviations or more below the mean peak bone mass (average of young and healthy adults) as measured by DXA. In some embodiments, diminished bone mass in a lower limb is a bone mineral density that is 2.2 standard deviations or more below the mean peak bone mass (average of young and healthy adults) as measured by DXA. In some embodiments, diminished bone mass in a lower limb is a bone mineral density that is 2.5 standard deviations or more below the mean peak bone mass (average of young and healthy adults) as measured by DXA.

In some embodiments, provided herein a method based on the notion that calibration of a protuberance including a rotating or vibrating protuberance supporting an area under a subject foot inhibits mineral loss in a nearby bone. In some embodiments, provided herein a method based on the notion that calibration of a rotating or vibrating protuberance supporting an area under a subject foot increases the density in a nearby bone. In some embodiments, calibrating a protuberance may include calibrating convexity, calibrating height, calibrating weight, calibrating position, calibrating resilience or any combination thereof may include a therapeutic effect according to the methods described herein. In some embodiments, calibration may include setting the vibration i.e. magnitude, frequency, etc. Calibrating both an anterior protuberance and a posterior protuberance, in a subject in need thereof, according to the disclosed embodiments may include a therapeutic effect such as treating osteoporosis or osteopenia as described herein. In some embodiments, placement and calibration of a protuberance may include the induction of a differential interference during limb locomotion, gait, standing, running, or walking which may provide a favorable therapeutic effect according to the methods described herein. In some embodiments, the term "interference" may include disturbance, interruption, interposition, perturbation, obstruction, or any combination thereof. In some embodiments, the ability to fine-tune an induced rotating/vibrating interference under a foot of a subject afflicted with low bone density may result in treating a disease (such as osteoporosis) or alleviating pain stemming from the disease. In some embodiments, provided herein a method of treating a patient suffering from bone loss/pain by specific placement of at least two calibrated, differential, rotating/vibrating disturbances or protuberances under the patient's feet. In some embodiments, the terms "patient" and "subject" are used interchangeably.

In some embodiments, provided herein that the posterior protuberance is a bulbous protuberance. In some embodiments, provided herein that the anterior protuberance is a bulbous protuberance. In some embodiments, provided herein that both the posterior protuberance and the anterior protuberance are bulbous protuberances.

In some embodiments, provided herein a method of treating osteoporosis/osteopenia. The method may include a first step of securing a footwear device (or simply "the device") to a subject's foot, whereby the device may include a foot securing mean, a support member operably attached to the securing mean, and a moveable anterior protuberance and a moveable posterior protuberance. The method may include a second step of calibrating the posterior protuberance and the anterior protuberance to a balanced position. The balanced position may include a position whereby the device provides a reduced inversion or a reduced eversion to the subject's foot during the stance phases. The method may include a third step of fixing the posterior protuberance and the anterior protuberance to the support member in the balanced position.

In some embodiments, low bone density and the pathologies associated with same may result in a gait disorder. Both the gait disorder and the pathologies associated with low bone density are treatable according to the methods described herein.

In some embodiments, a subject is a human subject. In some embodiments, a subject is a human subject afflicted with osteoporosis or osteopenia. In some embodiments, a subject is a human subject afflicted with a pathology stemming from low bone density such as osteoporosis and osteopenia.

In some embodiments, inhibiting the deterioration in bone density or increasing bone density may result in reducing the risk of fractures. In some embodiments, inhibiting the deterioration in bone density or increasing bone density may result in diminishing, alleviating, reducing, inhibiting, improving, reversing, and/or ameliorating: pain, stiffness, swelling, inflammation, cartilage degeneration, deterioration of neuro-muscular control, deterioration of proprioception bracing, pathological moments, gait disorders, limping, compensatory gait, antalgic gait, asymmetry in gait, guarding of muscles, loosening of ligaments, stretching of ligaments, stretching of joint capsule, reduced step length, reduced single limb support, increased single limb support, reduced gait velocity, or any combination thereof. In some embodiments, inhibiting the deterioration in bone density or increasing bone density may result in diminishing, alleviating, reducing, inhibiting, improving, reversing, and/or ameliorating subchondral bone changes, bone softening, or any combination thereof.

In some embodiments, inhibiting the deterioration in bone density or increasing bone density may include performing a variety of maneuvers in a proprioceptive and/or kinesthetic exercise plan for the foot, leg, upper leg, lower back and even upper torso and other body parts and organs. In some embodiments, inhibiting the deterioration in bone density or increasing bone density may include performing a variety of walking and or gait exercise plan for the foot, upper leg, lower back and even upper torso and other body parts and organs.

In some embodiments, the subject is at risk of fractures or already suffering from fractures. In some embodiments, fractures are in bones within the lower limb. In some embodiments, a fracture is in the form of cracking (as in a hip fracture) or collapsing (as in a compression fracture of the vertebrae of the spine). In some embodiments, a fracture is a spine fracture, hip fracture, or rib fracture. In some embodiments, a fracture is can occur in almost any skeletal bone.

Osteoporosis

In some embodiments, osteoporosis may include the presence of a fragility fracture. In some embodiments, osteoporosis is primary type 1, primary type 2, or secondary. In some embodiments, a subject according to the disclosed methods, assemblies and devices is a woman after menopause also referred to as primary type 1 or postmenopausal osteoporosis.

In some embodiments, the disclosed methods may reduce "osteoporosis risks" such as fractures. In some embodiments, the disclosed methods may be unexpectedly effective for treating osteoporosis and for reducing osteoporosis risks by toning deambulatory muscles, improving proprioception, equilibrium, and increasing bone density.

In some embodiments, the disclosed methods may reduce the risk of debilitating acute and chronic pain in the elderly which is often attributed to fractures from osteoporosis and can lead to further disability and early mortality. In some embodiments, the disclosed methods may reduce the risk of asymptomatic fractures. In some embodiments, the disclosed methods may treat and/or reduce the risk of a vertebral collapse ("compression fracture") and sudden back pain and/or radiculopathic pain associated with same. In some embodiments, the disclosed methods may treat and/or reduce the risk of spinal cord compression or cauda equina syndrome. In some embodiments, the disclosed methods may treat and/or reduce the risk of vertebral fractures and/or stooped posture. In some embodiments, the disclosed methods may treat and/or reduce the risk of loss of height, and chronic pain with resultant reduction in mobility.

In some embodiments, the disclosed methods may treat and/or reduce the risk of fractures of the long bones which acutely impair mobility. In some embodiments, the disclosed methods may treat and/or reduce the risk of hip fracture and complications resulting from same such as deep vein thrombosis and pulmonary embolism.

Pain

In some embodiments, "pain" as used herein may include a sharp ache. In some embodiments, "pain" as used herein may relate to burning sensation in the associate muscles and tendons. In some embodiments, "pain" as used herein may relate to continuous pain. In some embodiments, "pain" as used herein may relate to a momentary pain. In some embodiments, "pain" as used herein may relate to seasonal pain (winter, summer or change of weather). In some embodiments, "pain" as used herein may relate to activity specific pain such as sports or any other physical activity related pain. In some embodiments, pain may relate to a spinal pain as described herein.

Treatment

In some embodiments, the method as described herein may involve exercise with the device as described herein. In some embodiments, exercise may relate to walking or any other form of gait movement. In some embodiments, improvement may relate to gait improvement, measured in a gait lab. In some embodiments, improvement results in higher bone density compared to the starting point (prior to treatment or the day before treatment). In some embodiments, improvement in subject's physical state is observed by using the methods described herein. In some embodiments, treating may relate to improvement in subject's physiological state. In some embodiments, treating may relate to improvement in subject's mental state. In some embodiments, treating may relate to improvement in subject's wellbeing. In some embodiments, treating may relate to relieving pain such as described herein. In some embodiments, treating may relate to reducing the risk of fractures. In some embodiments, treating may relate to inducing de-novo bone build-up. In some embodiments, treating may relate to increasing movement. In some embodiments, treating may relate to increasing movement secondary to pain.

In some embodiments, treating may relate to inhibiting regional muscles atrophy. In some embodiments, treating may relate to reversing regional muscles atrophy. In some embodiments, treating may relate to inducing muscle build-up. In some embodiments, treating may relate to inducing differential muscle build-up. In some embodiments, treating may relate to increasing bone mineral density. In some embodiments, treating may relate to increasing bone mineral density in a bone described herein. In some embodiments, treating may relate to increasing bone mineral density in a target bone to less than 2.5 standard deviations below the mean peak bone mass (average of young and healthy adults) as measured by DXA. In some embodiments, treating may relate to increasing bone mineral density in a target bone to less than 2.0 standard deviations below the mean peak bone mass (average of young and healthy adults) as measured by DXA. In some embodiments, treating may relate to increasing bone mineral density in a target bone to less than 1.8 standard deviations below the mean peak bone mass (average of young and healthy adults) as measured by DXA. In some embodiments, treating may relate to increasing bone mineral density in a target bone to less than 1.5 standard deviations below the mean peak bone mass (average of young and healthy adults) as measured by DXA. In some embodiments, treating may relate to increasing bone mineral density in a target bone to less than 1.0 standard deviations below the mean peak bone mass (average of young and healthy adults) as measured by DXA. In some embodiments, treating may relate to increasing bone mineral density in a target bone to less than 0.5 standard deviations below the mean peak bone mass (average of young and healthy adults) as measured by DXA. In some embodiments, a target bone may be a bone susceptible to fractures as described herein such as but not limited to hip bone. In some embodiments, a target bone may be a bone susceptible to fractures due to osteoporosis as described herein such as but not limited to hip bone.

In some embodiments, increasing bone mineral density may relate to improving gait. In some embodiments increasing bone mineral density may relate to improving balance. In some embodiments, increasing bone mineral density may relate to improving impairments of proprioception, balance, mobility, muscle strength, or any combination thereof.

In some embodiments, increasing bone mineral density may relate to manipulating a step length. In some embodiments, increasing bone mineral density may relate to decreasing "step length difference". In some embodiments, increasing bone mineral density may relate to manipulating single limb support. In some embodiments, increasing bone mineral density may relate to manipulating out/in towing angle. In some embodiments, increasing bone mineral density may relate to calibrating gait cycle (towards 40:40:20). In some embodiments, increasing bone mineral density may relate to manipulating cadence. In some embodiments, increasing bone mineral density may relate to manipulating the center of pressure (COP). In some embodiments, increasing bone mineral density may relate to correcting mean hip motion, knee motion, ankle motion, or any combination thereof in the sagittal, frontal, and transverse planes. In some embodiments, increasing bone mineral density may relate to improving walking pace or speed. In some embodiments, increasing bone mineral density may relate to enhancing walking pace or speed.

In some embodiments, improving walking pace or speed may relate to reaching a goal of walking speed of 1.6-4 km/hour. In some embodiments, improving walking pace or speed may relate to reaching a goal of walking speed of 1.6-4 km/hour for at least 2 minutes. In some embodiments, improving walking pace or speed may relate to reaching a goal of walking speed of 1.6-4 km/hour for at least 5 minutes. In some embodiments, improving walking pace or speed may relate to reaching a goal of walking speed of 1.6-4 km/hour for at least 10 minutes. In some embodiments, improving walking pace or speed may relate to reaching a goal of walking speed of 1.6-4 km/hour for at least 15 minutes. In some embodiments, improving walking pace or speed may relate to reaching a goal of walking speed of 2-3.5 km/hour for at least 2 minutes. In some embodiments, improving walking pace or speed may relate to reaching a goal of walking speed of 2-3.5 km/hour for at least 5 minutes. In some embodiments, improving walking pace or speed may relate to reaching a goal of walking speed of 2-3.5 km/hour for at least 10 minutes. In some embodiments, improving walking pace or speed may relate to reaching a goal of walking speed of 2-3.5 km/hour for at least 15 minutes. In some embodiments, improving walking pace or speed may relate to reaching a goal of walking speed of 2.5-3.2 km/hour for at least 2 minutes. In some embodiments, improving walking pace or speed may relate to reaching a goal of walking speed of 2.5-3.2 km/hour for at least 5 minutes. In some embodiments, improving walking pace or speed may relate to reaching a goal of walking speed of 2.5-3.2 km/hour for at least 10 minutes. In some embodiments, improving walking pace or speed may relate to reaching a goal of walking speed of 2.5-3.2 km/hour for at least 15 minutes.

In some embodiments, increasing bone mineral density may reduce the risk of fractures. In some embodiments, the methods as described herein may further include a combination treatment which may include the use of the device as described herein and a proper medication. In some embodiments, one of skill in the art will readily diagnose and prescribe the proper medication to a subject suffering from a disease or a condition such as described herein. In some embodiments, the medication is an analgesic such as acetaminophen.

In some embodiments, the outcome of treatment which is reducing the risk of fractures and increasing bone mineral density as provided herein may be apparent immediately after the initial use of the device as described herein. In some embodiments, the outcome of treatment as provided herein may be apparent after 10-1000000 meters of walking with the device as described herein. In some embodiments, the outcome of treatment as provided herein may be apparent after 50-100000 meters of walking with the device as described herein. In some embodiments, the outcome of treatment as provided herein may be apparent after 500-10000 meters of walking with the device as described herein. In some embodiments, the outcome of treatment as provided herein may be apparent after 500-5000 meters of walking with the device as described herein. In some embodiments, the outcome of treatment as provided herein may be apparent after 500-3000 meters of walking with the device as described herein. In some embodiments, the process of increasing bone mineral density as provided herein may be coupled to the actual use of the device as described herein.

In some embodiments, differential lower limbs load alteration may be the key for increasing bone mineral density. In some embodiments, differential muscle build-up may contribute to the process of increasing bone mineral density and may include inducing muscle build-up in regions of muscles atrophy.

In some embodiments, a device as disclosed herein may have an immediate effect with regard to pain stemming from the devastating process decrease in bone mineral density and/or fractures. In some embodiments, decreased bone mineral density induces crippled gait/walking. In some embodiments, a short term immediate effect (with respect to defective gait) may be apparent in a barefoot subject after walking with the device for 1-5 minutes. In some embodiments, short term immediate effect may be apparent in a barefoot subject after walking with the device for 30-600 minutes. In some embodiments, short term immediate effect may be apparent in a barefoot subject after walking with the device for 1-10 hours (hrs).

In some embodiments, short term immediate effect may be apparent in a barefoot subject after walking with the device for 5-1000 hours (hrs). In some embodiments, short term immediate effect may be apparent in a barefoot subject after walking with the device for 12-96 hours (hrs). In some embodiments, short term immediate effect may be apparent in a barefoot subject after walking with the device for 1-10 days. In some embodiments, short term immediate effect may be apparent in a barefoot subject after walking with the device for 7-21 days. In some embodiments, short term immediate effect may be apparent in a barefoot subject after walking with the device for 5-30 days.

In some embodiments, the term "effect" may include increasing bone mineral density. In some embodiments, the term "effect" may include reducing pain caused decrease in bone mineral density/fractures. In some embodiments, the term "treating" may include increasing bone mineral density/reducing the risk of fractures. In some embodiments, the term "treating" may include reducing pain directly or indirectly caused by a decrease in bone mineral density.

In some embodiments, the effect may be apparent in a barefoot subject after walking with the device for 1-2 months. In some embodiments, the effect may be apparent in a barefoot subject after walking with the device for 1-24 months. In some embodiments, the effect may be apparent in a barefoot subject after walking with the device for 2-6 months. In some embodiments, the effect may be apparent in a barefoot subject after walking with the device for 4-10 months. In some embodiments, the effect may be apparent in a barefoot subject after walking with the device for 6-48 months. In some embodiments, the effect may be apparent in a barefoot subject after walking with the device for 12-24 months. In some embodiments, the effect may be apparent in a barefoot subject after walking with the device for 10-30 months.

In some embodiments, treating may be a process wherein the subject's disease or condition is ameliorated. In some embodiments, treating may be improvement over time. In some embodiments, treating may be continuous improvement over time. In some embodiments, progress or improvement may be reduction in any measure provided herein. In some embodiments, progress or improvement may be measured in a gait lab. In some embodiments, progress or improvement may be measured by radiological methods. In some embodiments, radiological methods for measuring progress, treatment and/or improvement may be known to one of skill in the art (such as but not limited to: X-ray, MRI, etc.). In some embodiments, progress or improvement may be measured by a pain questionnaire. In some embodiments, progress or improvement may be measured by physical examination that includes examining a range of motions. In some embodiments, progress or improvement may be measured by visual clinical gait assessment. In some embodiments, progress or improvement may be measured by methods for measuring bone density. In some embodiments, methods for measuring bone density may be known to one of skill in the art.

In some embodiments, a device as described herein may be prescribed to a subject according to the subject's physical condition. In some embodiments, a device as described herein may be prescribed to a subject according to the subject's medical condition. In some embodiments, a device as described herein may be prescribed to a subject according to the subject's medical history. In some embodiments, prescription may include directions of how to use the device. In some embodiments, prescription may include intensity of use, daily use, or daily distance directions.

In some embodiments, prescription to a subject having step length of 45 cm or less may include usage of the device by walking for 10-40 minutes a day. In some embodiments, prescription to a subject having step length of 45 cm or less may include usage of the device by walking for 10-40 minutes every other day.

In some embodiments, medium prescription may apply to subjects having step length of 45-60 cm. In some embodiments, medium prescription may apply to subjects having step length of 50-60 cm. In some embodiments, medium prescription may apply to subjects having step length of 60-65 cm. In some embodiments, medium prescription may include usage of the device by walking for 5-20 minutes a day. In some embodiments, medium prescription may include usage of the device by walking for 10-20 minutes a day. In some embodiments, medium prescription may include usage of the device by walking for 5-15 minutes a day.

In some embodiments, high prescription may apply to subjects having step length of 65 cm and above. In some embodiments, high prescription may apply to subjects having step length of 60 cm and above. In some embodiments, high prescription may include usage of the device by walking for 5-20 minutes a day. In some embodiments, high prescription may include usage of the device by walking for 10-20 minutes a day. In some embodiments, high prescription may include usage of the device by walking for 5-15 minutes a day.

In some embodiments, any prescription as described herein may include increase in daily usage time as the subject's step length improves. In some embodiments, any prescription as described herein may include increase in daily usage time as the subject's functional level improves. In some embodiments, any prescription as described herein may include increase in daily usage time as subject's pain decreases. In some embodiments, any prescription as described herein may include increase in daily usage time as subject's disease or condition as described herein, improves. In some embodiments, a prescription as described herein may further include medicating the subject according to his or hers medical condition.

In some embodiments, a prescription as described herein may further include adjustments of the device as subject's disease or condition improves or deteriorates. In some embodiments, adjustments of the device for increasing bone density may include calibrating or positioning a protuberance as described herein. In some embodiments, the phrases "bone density" and "bone mineral density" are used interchangeably.

Footwear Device

The footwear device may be secured to a subject's foot. The term "secured to a subject's foot" may relate to securing the device to a foot of the subject directly or securing the device to any footwear such as but not limited to shoes, boots, etc. that are secured to a subject's foot. For example, the footwear device may include footwear, thus enabling the footwear device to be secured to the foot of the subject directly. A foot securing means may secure the device to a subject's foot while various different feet securing means may be used. The foot securing mean may include a plurality of securing means. In some embodiments, the foot securing mean may include a lace. In some embodiments, a foot securing mean may include a Velcro fastener. In some embodiments, a foot securing mean may include securing straps.

The footwear device may include a support member, which may be secured to footwear or directly to the foot of the subject. The support member may be operably attached to the securing mean. The term "operably attached" may relate to sufficient attachment between the securing mean and the support member. The support member or footwear of the footwear device may include a sole or a sole assembly. In some embodiments, the support member may be a sole or a sole assembly. The sole assembly may include an insole, an outsole and/or midsole. In some embodiments, the support member may include an upper (i.e., the part of the shoe that is on top of the foot). In some embodiments, the upper may be operably attached to the securing mean (such as but not limited to laces). In some embodiments, the upper may include straps which may partially or totally enclose the foot. In some embodiments, the upper may include straps that function as securing means (such as sandals).

Reference is made to FIGS. 1-4, which illustrate an exemplary footwear device 10 (or simply "device 10") constructed and operative in accordance with an embodiment. Device 10 may be supplied as one or more pairs of shoe-like devices, or alternatively, as just one of the shoe-like devices. In some embodiments, footwear 10 may include a support member 12 having a periphery in a shape of a shoe sole comprising an upper surface 14. In the illustrated embodiment, the upper surface 14 may be indented, for example, with a peripheral ridge 16. In some embodiments, device 10 may be attached to a foot of a user by means of a boot 18 and/or fasteners 20, such as but not limited to, VELCRO straps, buckles, shoe laces, and the like. In some embodiments, device 10 may be attached to a foot of a user by means of a shoe. In some embodiments, a shoe may include a platform of a sneaker. In some embodiments, the term sneaker may include a boot. In some embodiments, the term sneaker may include a walking boot. In some embodiments, a shoe may include a platform of a running shoe. In some embodiments, a shoe may include a platform of an elegant shoe. In some embodiments, a shoe may include a platform of a walking shoe or boot.

In some embodiments, boot 18 may be fashioned for attachment to the user's foot with or without fasteners 20. In some embodiments, fasteners 20 may be used as foot securing means to attach device 10 to the user's foot without boot 18.

Protuberances

In some embodiments, device 10 may include protuberances 22 in a fixed position. Protuberances 22 may have any shape known to one of skill in the art. In some embodiments, device 10 may include at least two bulbous protuberances 22. In some embodiments, protuberance 22 may be symmetrical. In some embodiments, protuberance 22 may be asymmetrical. In some embodiments, protuberance 22 may include a shape of a: polygon, decagon, digon, dodecagon, nonagon, henagon hendecagon, heptagon, hexadecagon, hexagon icosagon, octagon, pentagon, triangle, Penrose tile, trapezium, isosceles, trapezium undecagon, quadrilateral, Lozenge, rhomboid, rectangle, square, rhombus, trapezoid, polydrafter, arbelos, circle, disc, circle, excircle, crescent, dome, ellipse, lune, oval, sphere, asteroid, or deltoid.

In some embodiments, each protuberance 22 may have a curved outer contour 26. In some embodiments, each protuberance 22 may have a different curved outer contour. In some embodiments, each protuberance 22 may have a convexity.

In some embodiments, protuberance 22 may include a dome shape. In some embodiments, protuberance 22 may include a dome shape which may further include multiple different convexities. In some embodiments, each protuberance 22 may include a different convexity. In some embodiments, each protuberance 22 may include a different set of convexities. The cross-section of the contour 26, that is, either the cross-section taken with respect to a longitudinal axis 28 (FIG. 4) of support member 12 (corresponding to the shape seen in FIG. 2) or the cross-section taken with respect to a latitudinal axis 30 (FIG. 4) of support member 12 (corresponding to the shape seen in FIG. 3), or any other cross-section, may have any curvilinear shape.

In some embodiments, each protuberance 22 comprises a base and a cap, wherein the base is fixed or configured to be fixed on a lower surface of the footwear. In some embodiments, each protuberance 22 comprises a base and a cap, wherein the base is fixed or configured to be fixed on a lower surface of the outsole. In some embodiments, each shoe within the device described herein comprises two bases wherein one base is positioned within the calcaneus support portion and the other base is positioned within the phalanges support portion. In some embodiments, positioned further includes fixed and/or fastened.

In some embodiments, a base and a cup rotatively align. In some embodiments, a cap is fixed into the base. In some embodiments, "fixed" is rotatively aligned. In some embodiments, the base is locked to the cap via a locking fixture configured to lock and unlock an alignment of the base and cap. In some embodiments, the locking fixture is positioned on the edge or the rim of the base. In some embodiments, the locking fixture is positioned on the edge or the rim of the cap. In some embodiments, the locking fixture comprises two portions wherein a first portion is located on the edge or the rim of the cap and the second portion is located on the edge or the rim of the base. In some embodiments, the base is stationary. In some embodiments, the cup is replaceable. In some embodiments, replacement of the cup does not shange the position of the base. In some embodiments, each cup has a different height.

In some embodiments, the cup is detached from the base (lock and unlock) via an alignment of a base and cap. In some embodiments, an alignment of a base and cap is within a single position within or on the: base, cap or both. In some embodiments, an alignment of a base and cap is when the position on the base and on the cap align. In some embodiments, a "position" for alignment (on the base, cap or both) is 0.05 to 2 cm long. In some embodiments, a "position" for alignment (on the base, cap or both) is 0.1 to 2 cm long. In some embodiments, a "position" for alignment (on the base, cap or both) is 0.1 to 1 cm long. In some embodiments, a "position" for alignment (on the base, cap or both) is 0.2 to 0.5 cm long. In some embodiments, a locking fixture locks and unlocks the cap-base only upon an alignment as described herein.

In some embodiments, a base comprises fastening fixture. In some embodiments, a fastening fixture is a screw or any other connecting element. In some embodiments, a "connecting element" connect the base to the lower surface or the outsole. In some embodiments, a "connecting element" fixes the base to the lower surface or the outsole. In some embodiments, a "connecting element" fixes the base to a pre-defined position on the lower surface or the outsole. In one embodiment, "sole assembly" is the outsole. In one embodiment, "sole assembly" is the insole. In one embodiment, "sole assembly" is both the outsole and the insole.

In some embodiments, the contours 26 may have the shape of a conic section, that is, the shape of a circle, ellipse, parabola or hyperbola. The various cross-sections of the contours 26 of protuberance 22 may be shaped identically or differently. In some embodiments, the shape of protuberance 22 may be defined by equal arches. In some embodiments, the shape of protuberance 22 may be defined by a variety of arches of different radiuses which are tangent to each other. In some embodiments, the shape of protuberance 22 may be symmetrical. In some embodiments, the shape of protuberance 22 may be asymmetrical. In some embodiments, protuberance 22 may be a bulbous protuberance.

In some embodiments, a device such as device 10 may support the foot of a subject only by two protuberances when the two protuberances may be placed on a ground surface. In some embodiments, a device such as device 10 may support the foot of a subject during stance only by the two protuberances when the two protuberances are placed on a ground surface. In some embodiments, only the two ground engaging surfaces of the protuberances (such as the peak or the surface facing the ground) may be in contact with a ground surface during stance. In some embodiments, only the ground engaging surface in each protuberance may be in contact with a ground surface during stance.

In some embodiments, at least two bulbous protuberances 22 may protrude from a bottom surface 24 of support member 12. In some embodiments, only two bulbous protuberances 22 may protrude from a bottom surface 24 of support member 12. In some embodiments, a bottom surface 24 of support member 12 is an outsole.

In some embodiments, the ground engaging parts of the device are only the protuberances. In some embodiments, during all phases of gait including the stance phase the protuberances may be the only parts of the device which are ground engaging. In some embodiments, during all phases of gait including the stance phase the protuberances are the only parts of the device which are in direct contact with the ground.

In some embodiments, a protuberance as described herein may be movable. In some embodiments, a protuberance as described herein may be fixed. In some embodiments, a protuberance as described herein may be mountable. In some embodiments, a protuberance as described herein may be replaceable. In some embodiments, a protuberance as described herein may be movable along the outer surface of the support member. In some embodiments, a protuberance as described herein may be movable along the outer surface of the outsole. In some embodiments, a protuberance as described herein may be positioned within the outer surface of the support member.

In some embodiments, a protuberance as described herein may be movable or translatable such as in a track (e.g., forwards, backwards, sideways or diagonally) and/or rotatable about its own or other axis, or a combination of such motions.

In some embodiments, a protuberance may be movable within a predefined area. In some embodiments, a protuberance may be movable within an area of 1 cm² to 18 cm². In some embodiments, a protuberance may be movable within an area of 1 cm² to 6 cm². In some embodiments, a protuberance may be movable within an area of 1 cm² to 4 cm². In some embodiments, a protuberance may be movable within an area of 2 cm² to 8 cm². In some embodiments, a protuberance may be movable within an area of 3 cm² to 6 cm². In some embodiments, a protuberance may be movable within an area of 4 cm² to 10 cm². In some embodiments, a protuberance may be movable within an area of 5 cm² to 18 cm². In some embodiments, a protuberance may be movable within an area of 4 cm² to 12 cm².

In some embodiments, a predefined area may be a circle. In some embodiments, a predefined area may be a square. In some embodiments, a predefined area may be an ellipse. In some embodiments, a predefined area may be a rectangle. In some embodiments, a predefined area may be quadrangular. In some embodiments, a predefined area may include any shape known to one of skill in the art. In some embodiments, a predefined area may be shapeless.

In some embodiments, a protuberance may be positioned anywhere on the support member. In some embodiments, a protuberance may be fixed anywhere on the support member. In some embodiments, a protuberance may be positioned and/or fixed anywhere within a predefined area. In some embodiments, the protuberance may be hooked to a track. In some embodiments, the protuberance may be connected to a track. In some embodiments, the protuberance may be connected to a track and may be movable along the track. In some embodiments, the protuberance may be connected to a track, may be movable along the track, and may be positioned and/or fixed anywhere along the track.

Figure 2:
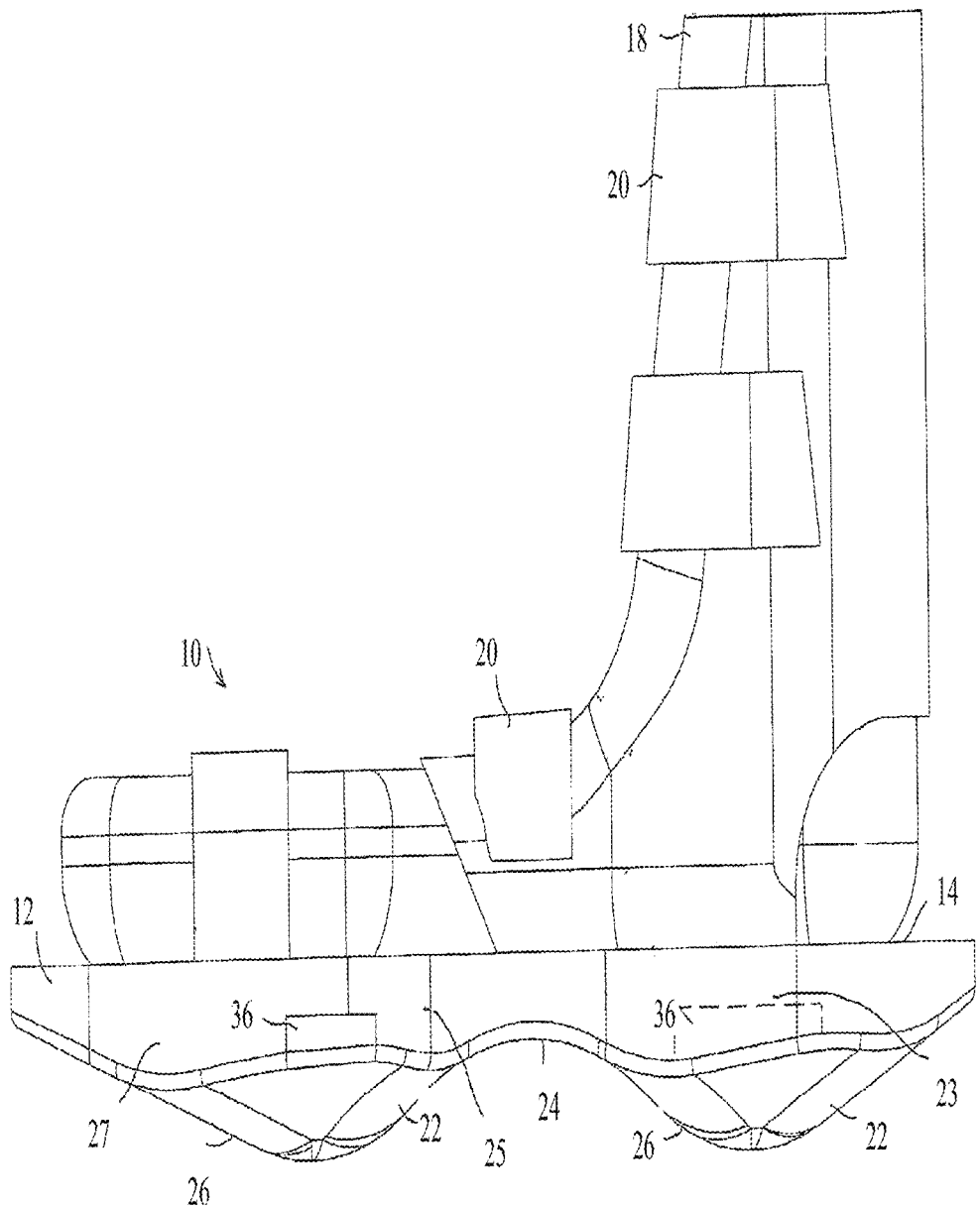
FIGS. 2 and 3 are simplified side-view and rear-view illustrations, respectively, of the footwear of FIG. 1.
Figure 3:
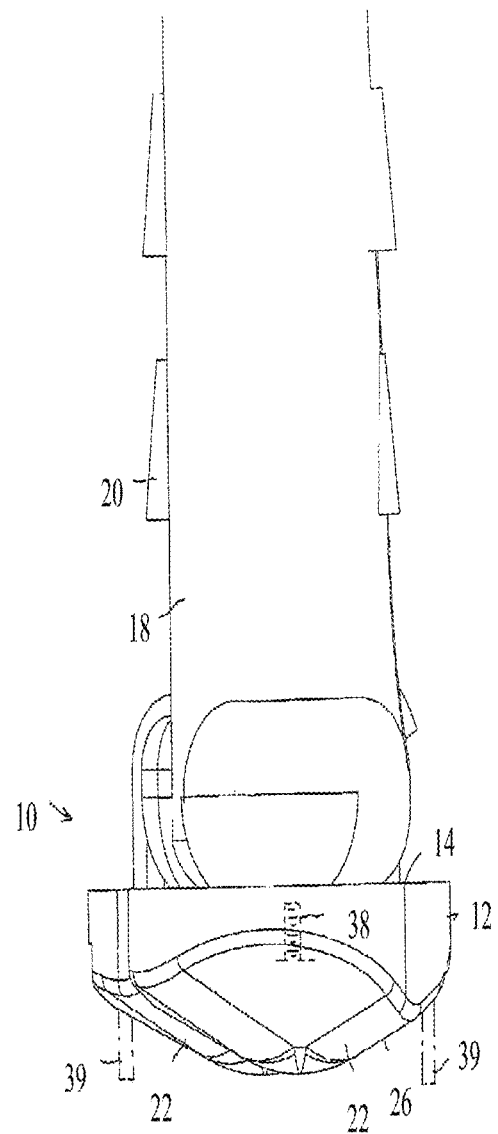

In some embodiments, a protuberance may be slidingly mounted on a support member. With reference to FIG. 2, a protuberance 22 may be mounted on a track 36 formed in bottom surface 24 of support member 12, and may be selectively positioned anywhere along track 36 and fastened and or fixed thereto. Track 36 may extend along a portion of the shoe sole or all along the length of the shoe sole. With reference to FIG. 3, alternatively or additionally, the amount of protrusion of protuberance 22 may be adjusted, such as by mounting protuberance 22 with a threaded fastener 38 to support member 12 and tightening or releasing threaded fastener 38. The term "fastening", "fixing" and "securing" may be used interchangeably.

In some embodiments, a device as described herein may further include an additional bulbous protuberance or bulbous protuberances, non-bulbous protuberance, such as non-bulbous protuberances 39 shown in FIG. 3. Protuberances 39 may be formed in the shape such as the shape of a peg, stud, bolt, pin, dowel and the like. Protuberances 39 may be rigid or flexible. Protuberances 39 may be of different resilience or hardness, such as having different elasticity properties or Shore hardness. Protuberances 39 may protrude by different amounts from bottom surface 24 of support member 12. The amount of protrusion of protuberances 39 or height may be adjusted. Protuberance 39 may be fixed or movable at any place on bottom surface 24 of support member 12.

In some embodiments, a protuberance may be slidingly mounted on a support member. In some embodiments, a device such as device 10 may include a sliding/shifting mechanism for a protuberance inside the sole of the device. In some embodiments, the sliding/shifting mechanism may include, without limitation, a mechanism that floats in a viscous matrix (e.g., fluid in a chamber formed in the sole), that is suspended by inner cables, or a niche trapping a protuberance with a fixing mean.

Fixing a Protuberance

As seen clearly in FIG. 2, one protuberance 22 may be positioned more posteriorly than the other protuberance 22. In some embodiments, a device as described herein may include at least one anterior protuberance. In some embodiments, a device as described herein may include at least one posterior protuberance. In some embodiments, the device may include one anterior protuberance and one posterior protuberance. In some embodiments, the device may include at least one anterior protuberance and one moveable posterior protuberance. In some embodiments, the device may include at least one moveable anterior protuberance and one posterior protuberance. In some embodiments, the device may include at least one moveable anterior protuberance and one moveable posterior protuberance. In some embodiments, the device may include one moveable anterior protuberance and one moveable posterior protuberance.

In some embodiments, the protuberances rise vertically and therefore each protuberance may include a base end and a peak end. In some embodiments, the surface area of the base may be larger than the surface area of the peak. In some embodiments, the peak may be the ground engaging portion of a protuberance in the stance phase. In some embodiments, the peak may be the ground engaging portion of a protuberance in all gait phases.

In some embodiments, a protuberance such as bulbous protuberance 22 may protrude from the upper surface 14 of support member 12.

Positions of Protuberance

In some embodiments, the actual position of the protuberances may enable load alterations that are essential for inducing increase in bone density. In some embodiments, the actual position of the protuberances may enable load alterations that are essential for inducing differential increase in bone density. In some embodiments, the actual position and characteristics (as described herein) of the protuberances may be set in a personalized manner according to the disease and the subject's personal posture.

Reference is now made, in one embodiment, to FIGS. 1-4, which illustrate footwear 10 constructed and operative in accordance with an embodiment of the present invention. Footwear 10, in one embodiment, may be supplied as one or more pairs of shoe-like devices, or alternatively, as just one of the shoe-like devices. In some embodiments, a shoe-like device may include a shoe platform and protuberances. Footwear 10, in one embodiment, may be designed to adapt on a shoe such as Footwear 10. Footwear 10, in one embodiment, may be a sandal or sandal-like footwear. In some embodiments, the shoe platform may be a boot. In some embodiments, the shoe platform may resemble a hiking boot.

In some embodiments, the footwear 10 may include a support member 12 having a periphery in a shape of a shoe sole with an upper surface 14. In some embodiments, the footwear 10 may include an insole placed on top of the upper surface 14. In some embodiments, the insole may be the interior bottom of footwear 10. In some embodiments, the insole may sit directly beneath the foot. In some embodiments, the insole is removable, replaceable, or both. In some embodiments, the insole may add comfort, control the shape, moisture, smell, or any combination thereof. In some embodiments, the insole may be placed to correct defects in the natural shape of the foot or positioning of the foot during standing or walking.

In some embodiments, support member 12 may include an outsole. In some embodiments, support member 12 may include bottom surface 24 or an outsole of support member 12. In some embodiments, bottom surface 24 or an outsole may be made of natural rubber or a synthetic imitation. In some embodiments, bottom surface 24 or an outsole may include a single piece, or may include separate pieces of different materials. In some embodiments, bottom surface 24 or an outsole may be softer or harder. In some embodiments, support member 12 may further include a midsole which may be a layer in between the outsole and the insole the most pressure down. In some embodiments, support member 12 may not have midsole.

In some embodiments, positioning at least a first bulbous protuberance and a second bulbous protuberance in a balanced position may be the position in which the footwear exerts the least valgus, varus, dorsal or plantar torque about the ankle in a subject being examined. In some embodiments, positioning at least a first bulbous protuberance and a second bulbous protuberance in a balanced position may be the position in which the footwear exerts the least valgus, varus, dorsal or plantar torque about the ankle in a subject being examined. In some embodiments, positioning at least a first bulbous protuberance and a second bulbous protuberance in a balanced position may be the position in which the footwear may provide the least or minimal lower limbs muscle activity. In some embodiments, positioning at least a first bulbous protuberance and a second bulbous protuberance in a balanced position may be the position in which the footwear provides balanced lower limbs muscle activity. In some embodiments, positioning at least a first bulbous protuberance and a second bulbous protuberance in a balanced position may be toning lower limb muscles. In some embodiments, positioning at least a first bulbous protuberance and a second bulbous protuberance in a balanced position may be toning the amount of tension or resistance to movement in a muscle involved in gait. In some embodiments, positioning at least a first bulbous protuberance and a second bulbous protuberance in a balanced position may be lower limb unloading that allows maximal ankle, knee, and hip joint mobility. In some embodiments, positioning at least a first bulbous protuberance and a second bulbous protuberance in a balanced position may be providing a reduction of muscle activity, larger passive ankle excursion, improved gait ability, or any combination thereof. In some embodiments, positioning at least a first bulbous protuberance and a second bulbous protuberance in a balanced position may be increasing stride length, stance symmetry, or a combination thereof. In some embodiments, positioning at least a first bulbous protuberance and a second bulbous protuberance in a balanced position may be increasing the length of the force point of action in lower limb muscles such as but not limited to: soleus, tibialis posterior, and both gastrocnemius muscles. In some embodiments, positioning at least a first bulbous protuberance and a second bulbous protuberance in a balanced position is toning the plantar flexors. In some embodiments, positioning at least a first bulbous protuberance and a second bulbous protuberance in a balanced position is preventing excessive forward rotation as the body moves forward over the stationary foot. In some embodiments, positioning at least a first bulbous protuberance and a second bulbous protuberance in a balanced position may be toning the push off of the heel.

Figure 4:
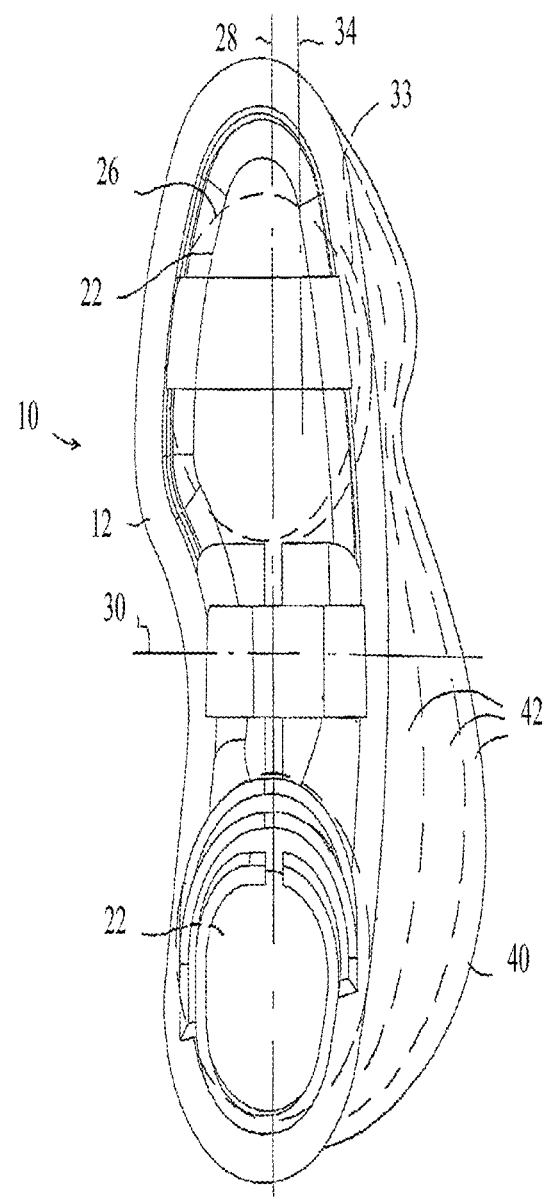
FIG. 4 is a simplified top-view illustration of the footwear of FIG. 1, showing further features of other embodiments.

In some embodiments, as seen in FIG. 4, the protuberances may be positioned on a common longitudinal axis of support member 12, such as the centerline 28 of support member 12. In some embodiments, the protuberances may be positioned on opposite sides of the latitudinal midline 30. In some embodiments, the protuberances may be positioned offset from the centerline 28 of support member 12, and on opposite sides of the latitudinal midline 30. In some embodiments, the bases of the protuberances may be positioned on the centerline of the support member. In some embodiments, the peaks of the protuberances may be positioned on opposite sides of the centerline of support member. In some embodiments, the meaning of "protuberance may be positioned offset from the centerline" may include that the peak or the ground engaging surface of a protuberances may be positioned offset from the centerline. In some embodiments, the meaning of "protuberance may be positioned offset from the centerline" may include that only the peak or the ground engaging surface of a protuberances may be positioned offset from the centerline but the centerline still may cross the protuberance.

In some embodiments, the peak or the ground engaging surface of the anterior protuberance may be positioned laterally from the centerline of the support member. In some embodiments, the peak or the ground engaging surface of the anterior protuberance may be positioned medially from the centerline of the support member. In some embodiments, the peak or the ground engaging surface of the anterior protuberance may be positioned laterally from the centerline of the support member and the peak or the ground engaging surface of the posterior protuberance may be aligned with centerline. In some embodiments, the peak or the ground engaging surface of the anterior protuberance may be positioned medially from the centerline of the support member and the peak or the ground engaging surface of the posterior protuberance may be aligned with centerline.

In some embodiments, the peak or the ground engaging surface of the posterior protuberance may be positioned laterally from the centerline of the support member. In some embodiments, the peak or the ground engaging surface of the posterior protuberance may be positioned medially from the centerline of the support member. In some embodiments, the peak or the ground engaging surface of the posterior protuberance may be positioned laterally from the centerline of the support member and the peak or the ground engaging surface of the anterior protuberance may be aligned with centerline. In some embodiments, the peak or the ground engaging surface of the posterior protuberance may be positioned medially from the centerline of the support member and the peak or the ground engaging surface of the anterior protuberance may be aligned with centerline.

In some embodiments, the peak or the ground engaging surface of the posterior protuberance may be positioned laterally from the centerline of the support member and the peak or the ground engaging surface of the anterior protuberance may be positioned medially from the centerline of the support member. In some embodiments, the peak or the ground engaging surface of the anterior protuberance may be positioned laterally from the centerline of the support member and the peak or the ground engaging surface of the posterior protuberance may be positioned medially from the centerline of the support member.

Figure 5:
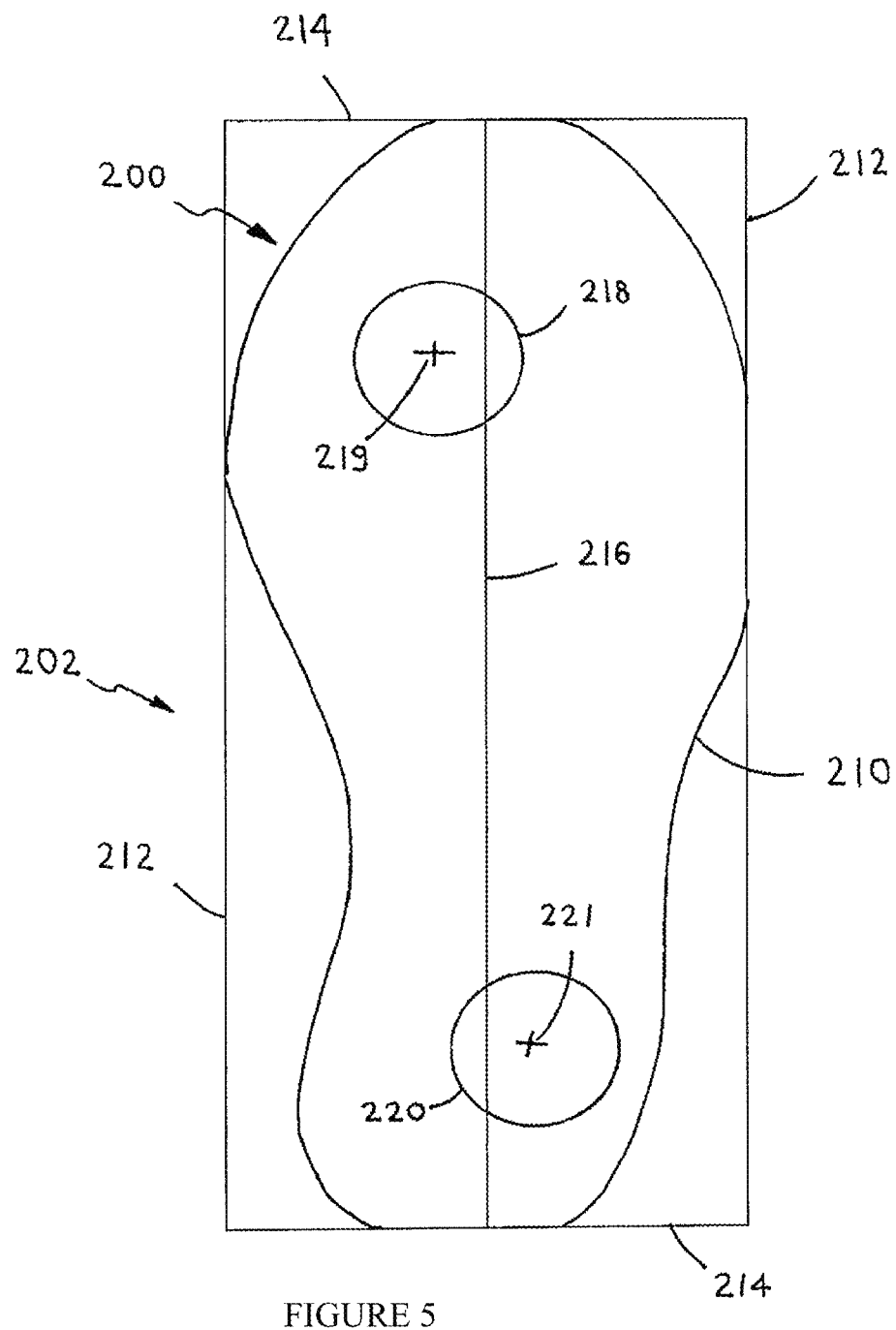
FIG. 5 is a simplified pictorial illustration of an alignment of the anterior (forward) and posterior (rearward) protuberances on a support member, according to some embodiments.
Figure 6:
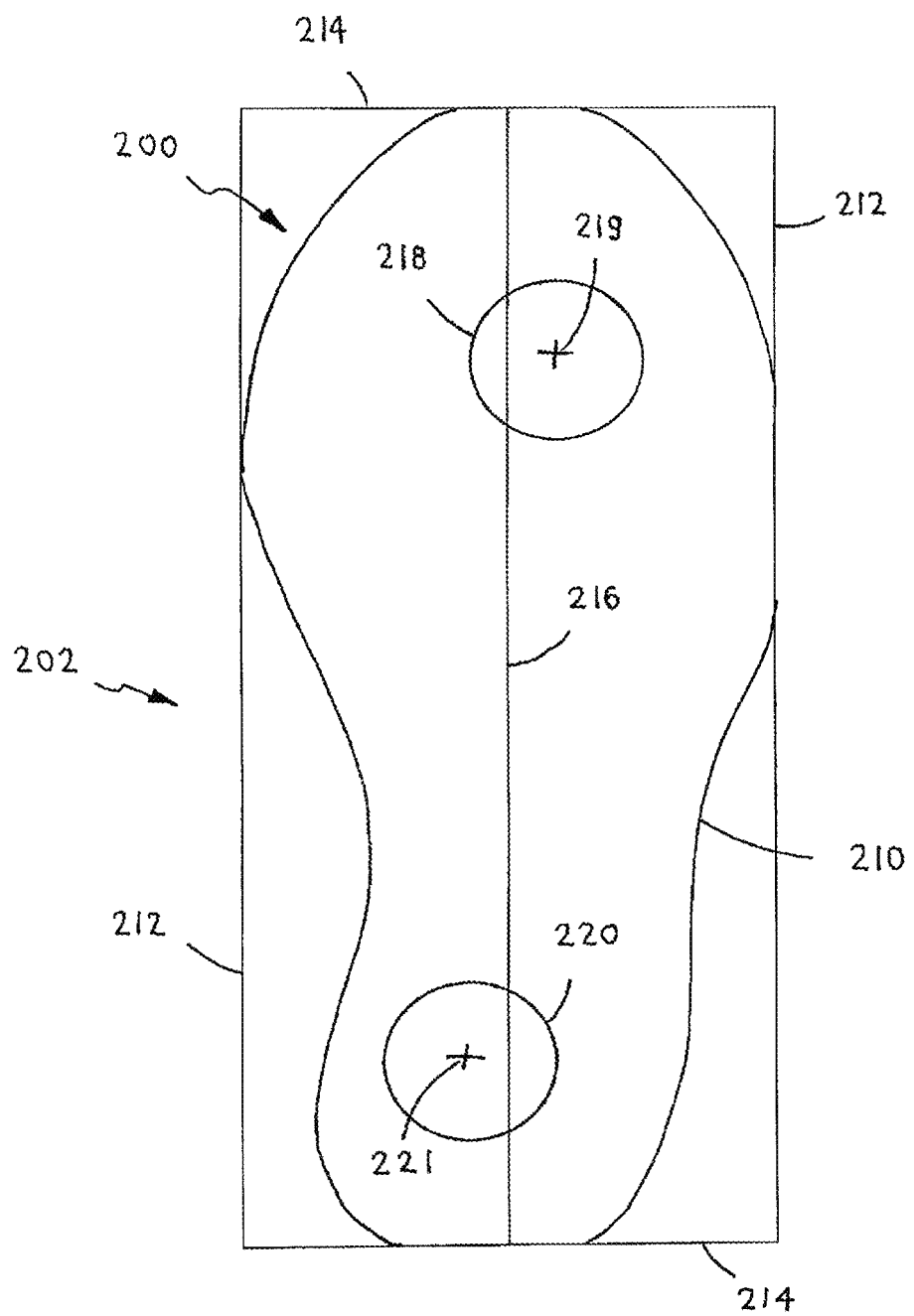
FIG. 6 is a simplified pictorial illustration of another alignment of the anterior and posterior protuberances on a support member, according to some embodiments.

In some embodiments, the centerline may divide longitudinally the calcaneus support portion into two equal halves and may further extend towards the phalanges and metatarsals support portion in a straight line. In some embodiments, the centerline may divide longitudinally the arch of the calcaneus support portion into two equal halves and may further extend towards the phalanges and metatarsals support portion in a straight line. In some embodiments, the centerline may divide longitudinally the proximal arch of the calcaneus support portion into two equal halves and may further extend towards the phalanges and metatarsals support portion in a straight line. In some embodiments, the centerline may divide longitudinally the support portion as seen in FIGS. 5-6 of the calcaneus support portion into two equal halves and may further extend towards the phalanges and metatarsals support portion in a straight line. In some embodiments of the present invention, the longitudinal centerline may be defined as a longitudinal straight line connecting middles of the short sides of a rectangle which delimits a contour of the support member.

In some embodiments, the bases of the protuberances may be positioned on the centerline of the support member and the peaks of the protuberances may be positioned on opposite sides of the centerline of the support member. In some embodiments, the bases of the protuberances may be positioned on the centerline of the support member but the peaks of the protuberances may be offset from the centerline of the support member. In some embodiments, the bases of the protuberances may be positioned on the centerline of the support member but the peaks of the protuberances may be positioned on opposite sides of the centerline of the support member. In some embodiments, positioning a protuberance may be positioning the peak or the ground engaging surface of a protuberance. In some embodiments, the terms "peak" and "ground engaging surface" may be used interchangeably.

In some embodiments, the anterior protuberance may be positioned medially from the centerline of the support member. In some embodiments, the peak of the anterior protuberance may be positioned medially from the centerline of the support member. In some embodiments, the base of the anterior protuberance may be position on the centerline of the support member but the peak of the anterior protuberance may be positioned medially from the centerline of the support member. In some embodiments, the anterior protuberance is may be positioned laterally from the centerline of the support member. In some embodiments, the peak of the anterior protuberance may be positioned laterally from the centerline of the support member. In some embodiments, the base of the anterior protuberance may be position on the centerline of the support member but the peak of the anterior protuberance may be positioned laterally from the centerline of the support member. In some embodiments, the posterior protuberance may be positioned medially from the centerline of the support member. In some embodiments, the peak of the posterior protuberance may be positioned medially from the centerline of the support member. In some embodiments, the base of the posterior protuberance may be positioned on the centerline of the support member but the peak of the posterior protuberance may be positioned medially from the centerline of the support member. In some embodiments, the posterior protuberance may be positioned laterally from the centerline of the support member. In some embodiments, the peak of the posterior protuberance may be positioned laterally from the centerline of the support member. In some embodiments, the base of the posterior protuberance may be positioned on the centerline of the support member but the peak of the posterior protuberance may be positioned laterally from the centerline of the support member.

In some embodiments, as seen in FIG. 2, posterior protuberance 22 may be positioned generally underneath a calcaneus (heel, ankle) support portion 23 of support member 12. In some embodiments, anterior protuberance 22 may be positioned generally underneath a metatarsals support portion 25 and/or phalanges support portion 27 of support member 12.

In some embodiments, as indicated by broken lines 33 in FIG. 4, the anterior protuberances 22 may be aligned on a longitudinal axis with its peak offset from centerline 28, and the posterior protuberance 22 may be also aligned on a longitudinal axis with its peak offset from centerline 28 but to the opposite direction of posterior protuberance 22 with respect to centerline 28.

In some embodiments, FIG. 5 is a simplified pictorial illustration of an alignment of the anterior (forward) and posterior (rearward) protuberances on a support member 200, according to embodiments. Centerline 216, in the embodiment shown in FIG. 12 may be defined as a longitudinal straight line (median) that may connect the middles of short sides 214 of a rectangle 212, the long sides 212 of which are parallel to centerline 216, and which delimits the contour 210 of the support member. In embodiments of the present invention contour 210 may be the contour (254, see FIG. 7) of the foothold confined by the upper part (253, see FIG. 7) of the footwear (250, see FIG. 7), corresponding to the last which is used to form the footwear. In other embodiments, contour 210 may be the outermost contour of the footwear. In other embodiments, contour 210 may be the contour of the bottom surface of the sole of the footwear. In some embodiments, the terms "forward" and "anterior" may be used interchangeably. In some embodiments, the terms "rearward" and "posterior" may be used interchangeably.

According to embodiments of the present invention, as shown in FIG. 5, forward protuberance 218 at the anterior (phalanges) portion of the support member (i.e. its front portion) may be positioned medially offset to centerline 216. By "medially offset" is meant that a peak surface (which may be the ground engaging surface) of protuberance 218 (marked by cross 219) is shifted from centerline 216 medially towards the inner side of support surface 200, facing the support member of the other foot (not shown in this figure). The peak surface may be a surface on the protuberance which is furthest from the support surface with respect to other surfaces of the protuberance.

According to some embodiments, as shown in FIG. 5, rearward protuberance 220 at the posterior (calcaneus) portion of the support member (i.e. its back portion) may be positioned laterally offset to centerline 216. By "laterally offset" is meant that a peak surface (which can be the ground engaging surface) of protuberance 220 (marked by cross 221) is shifted from centerline 216 laterally towards the outer side of support surface 200, away from the support member of the other foot (not shown in this figure).

The alignment of the protuberances shown in FIG. 5 may be useful, for example, for exercising users with one or more of the following medical indications: medial compartment-knee osteoarthritis medial meniscus tear or damage, genu varus, patello-femoral pain syndrome, patello-femoral problem (malalignment), lateral collateral ligamental damage or tear, bone bruise MTP/MFC (AVN), low back pain, hip OA, hip labrum damage (TCM), trochanteric bursitis, pes ansenius bursitis, ankle instability (supination), achilles tendonitis and metatrsalgia.

FIG. 6 is a simplified pictorial illustration of another alignment of the anterior and posterior protuberances on a support member, according to some embodiments. According to some embodiments, as shown in FIG. 6, forward protuberance 218 may be laterally offset to centerline 216, whereas rearward protuberance 220 may be medially offset to centerline 216. The alignment of the protuberances shown in FIG. 5 may be useful, for example, for exercising users with one or more of the following medical indications: lateral meniscus tear or damage, lateral compartment knee osteoarthritis, valgus knee (genu valgus), patello-femoral pain syndrome, patello-femoral problem (malalignment), MCL Ligament tear, bone bruise LTP/LFC (AVN), hip labrum damage or tear, hip pain, ankle instability (pronoation), achilles tendonitis, tibilias insufficiency or dysfunction and metatarsalgia.

Figure 7:
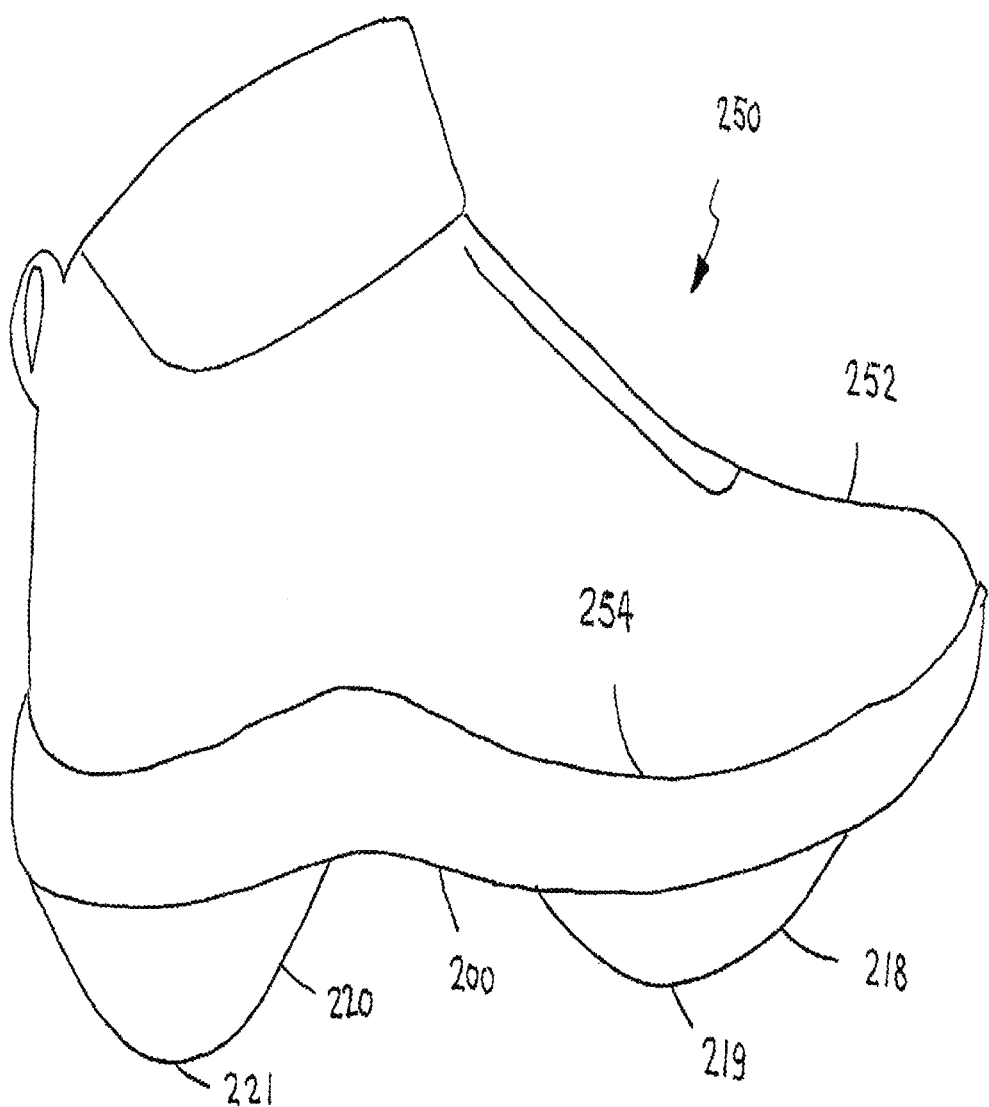
FIG. 7 is a simplified pictorial illustration of a sneaker constructed and operative in accordance with an embodiment, whose rearward protuberance may have a greater height than the height of the forward protuberance.

FIG. 7 is a simplified pictorial illustration of a sneaker 250 constructed and operative in accordance with an embodiment of the present invention, whose rearward protuberance 220 has a greater height than the height of the forward protuberance 218. It is noticeable that such arrangement may facilitate initial contact between rearward protuberance 220 and the supporting ground (not shown in this figure) when a user wears the sneaker, before the forward protuberance is brought in contact with the ground. When both protuberances are placed in contact with the ground the foot of the user wearing sneaker 250 may acquire a downward inclination with respect to direction of gait of the user.

Figure 8:
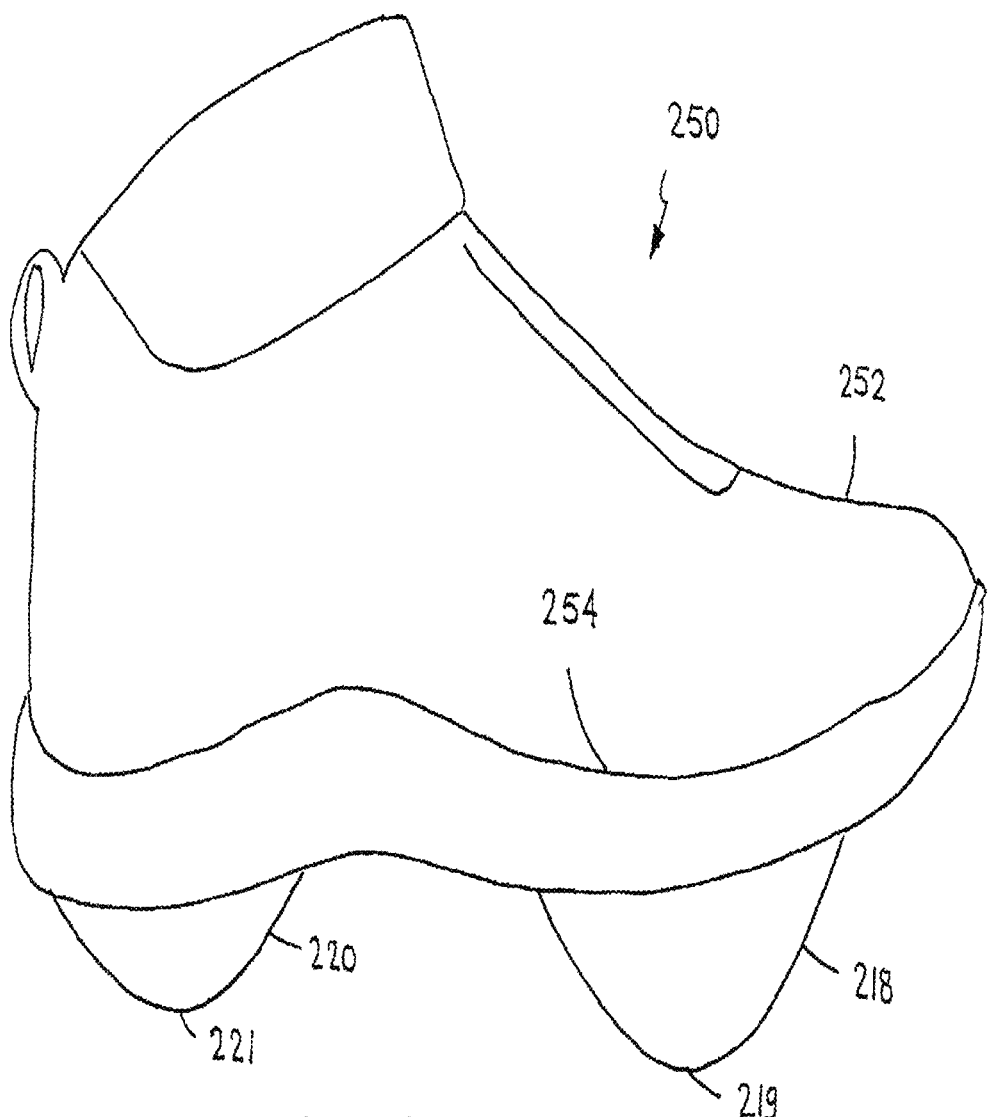
FIG. 8 is a simplified pictorial illustration of a sneaker constructed and operative in accordance with an embodiment, whose forward protuberance may have a greater height than the height of the rearward protuberance.

FIG. 8 is a simplified pictorial illustration of a sneaker 250 constructed and operative in accordance with an embodiment, whose forward protuberance 218 may have a greater height than the height of the rearward protuberance 220. In this embodiment when both protuberances are placed in contact with the ground the foot of the user wearing sneaker 250 may acquire an upward inclination (with respect to the direction of gait of the user.

Figure 9:
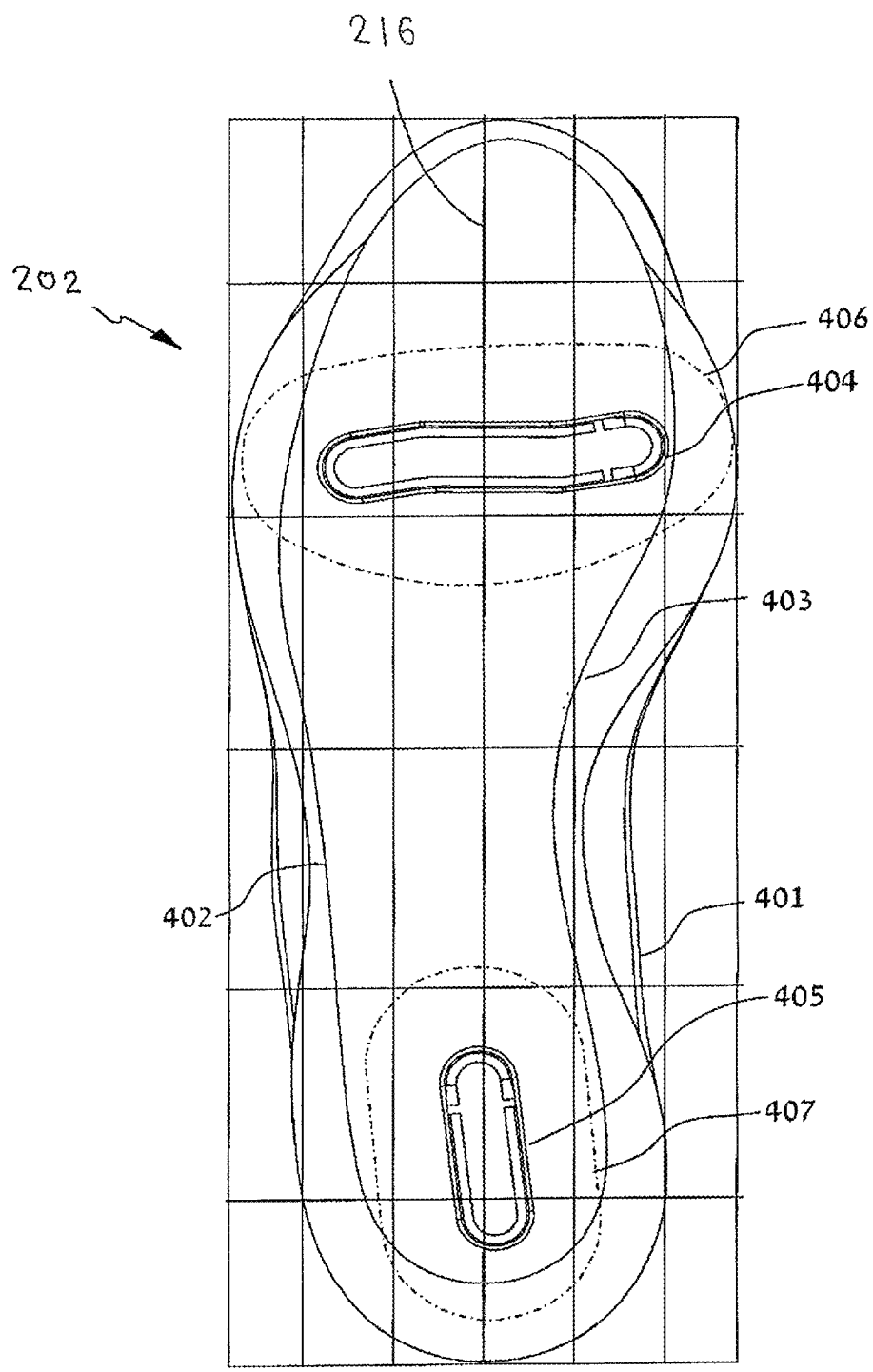
FIG. 9 illustrates maximal area boundaries of positioning of the anterior and posterior protuberances with respect to a support surface, according to some embodiments.

FIG. 9 illustrates maximal area boundaries of positioning of the anterior and posterior protuberances with respect to a support surface, according to some embodiments. Shown in this figure is a bottom view of a sneaker designed to be worn on a right foot of a user. The medial side may be thus the right side of the drawing, facing the arc of greater curvature of the side arcs of the sneaker. The lateral side may be opposite to the medial side that is the left side of the drawing, facing the arc of lesser curvature of the side arcs of the sneaker. Indicated are midsole 401 and last/shoe 402, contour 403 of the foothold which may be determined by the last used in the making of the sneaker. Front rail 404 and rear rail 405 may be used for anchoring the protuberance. The area bordered by dotted line 406 may mark the maximal area within which the peak surface of the anterior protuberance, i.e. the ground engaging surface of the anterior protuberance, may be located, according to some embodiments. The area bordered by dotted line 407 may mark the maximal area within which the peak surface of the posterior protuberance may be located.

Figure 10:
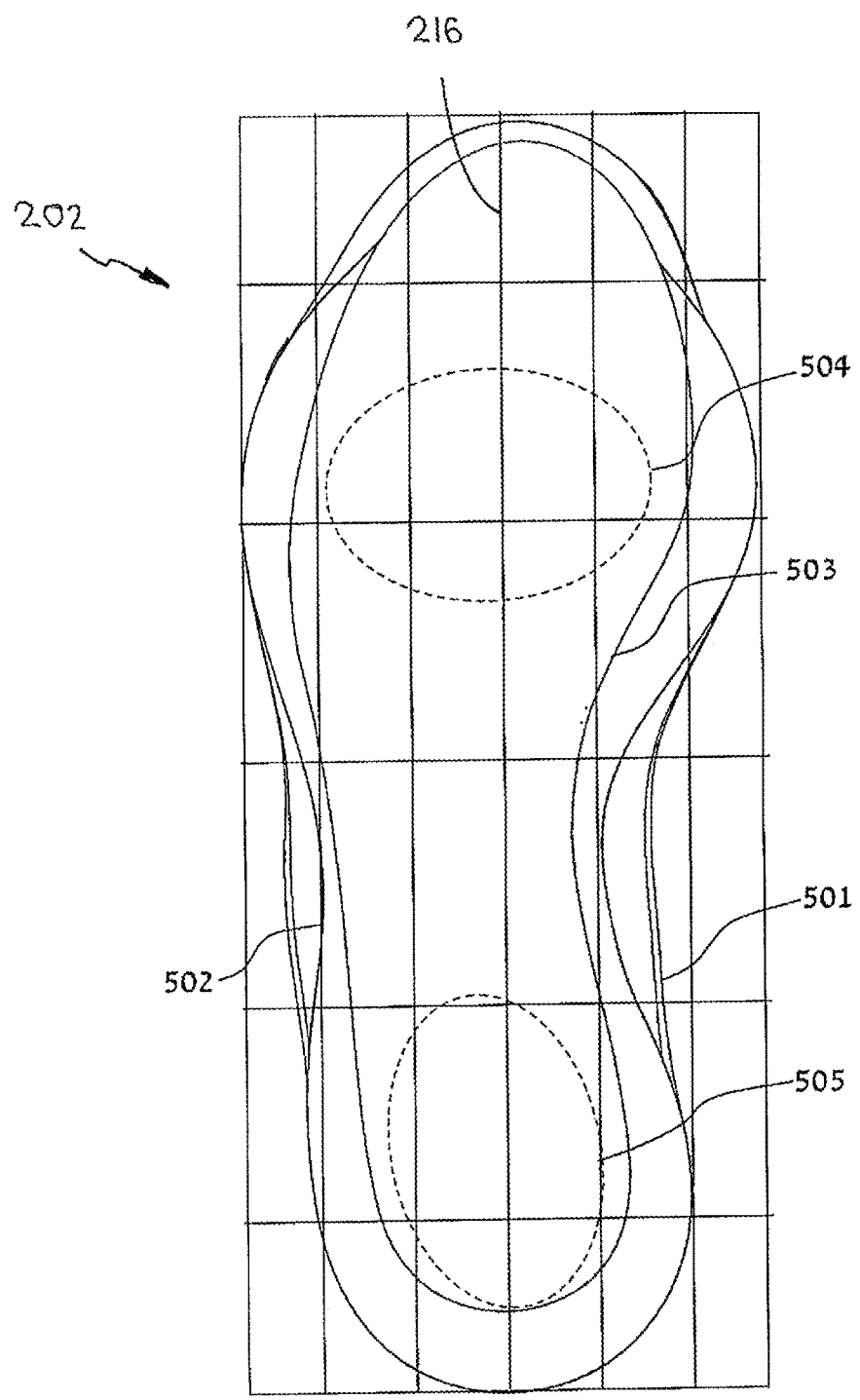
FIG. 10 illustrates effective area boundaries of positioning of the anterior and posterior protuberances with respect to a support surface, according to some embodiments.

FIG. 10 illustrates the effective area boundaries of positioning of the anterior and posterior protuberances with respect to a support surface, according to some embodiments. Indicated are the midsole 501 and outsole 502, contour 503 of the foothold which may be determined by the last used in the making of the sneaker. The area bordered by dotted line 504 may mark the effective area within which the peak surface of the anterior protuberance, i.e. the ground engaging surface of the anterior protuberance, may be located, according to some embodiments. The area bordered by dotted line 505 may mark the effective area within which the peak surface of the posterior protuberance. "Effective" may refer to the effectiveness of use of the footwear according to some embodiments, which may facilitate treatment.

For clarity both FIGS. 9 and 10 may be divided to 36 equal parts. The effective locations may be within the same parts regardless of sizing.

Figure 11:
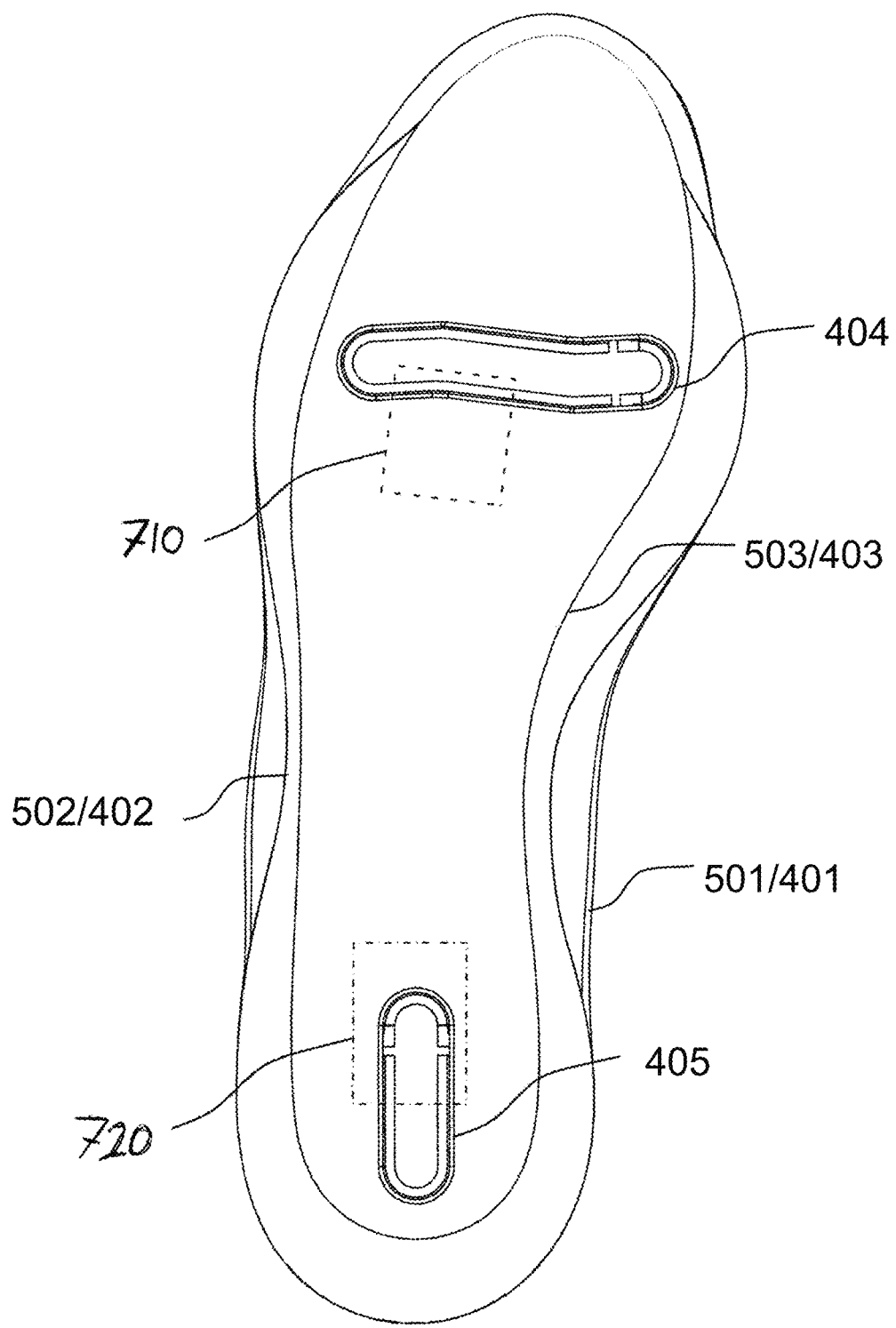
FIG. 11 illustrates effective area boundaries of positioning of the anterior and posterior protuberances with respect to a support surface, according to an embodiment.

FIG. 11 illustrates the effective area boundaries of positioning of the anterior and posterior protuberances with respect to a support surface, according to some embodiments which may include treatment and alleviating pain for the following diseases and/or conditions: Lateral meniscus tear/damage, Lateral compartment knee osteoarthritis, Valgus knee (genu valgus), Patello-femoral pain syndrome, Patello-femoral deficiency (mal-alignment), MCL Ligament tear, Bone bruise LTP/LFC (AVN), Hip labrum damage (tear), hip musculoskeletal pain, ankle instability (Pronoation), Achilles tendonitis, Tibilias insufficiency, Metatansalgia, or any combinations thereof. Indicated is the area bordered by dotted line 710 which may mark the effective area within which the peak surface of the anterior protuberance, i.e. the ground engaging surface of the anterior protuberance, may be located, while treating or alleviating pain for the diseases and/or conditions described for FIG. 11 hereinabove. Indicated is the area bordered by dotted line 720 which may mark the effective area within which the peak surface of the posterior protuberance, i.e. the ground engaging surface of the posterior protuberance, may be located, while treating or alleviating pain for the diseases and/or conditions described for FIG. 11 hereinabove. The areas bordered by dotted lines 710 and 720 may be within the areas bordered by dotted lines 504 and 505, respectively, in FIG. 10. As provided before, FIG. 10 may be divided to 36 equal parts. The effective locations may be within these effective parts regardless of sizing.

Figure 12:
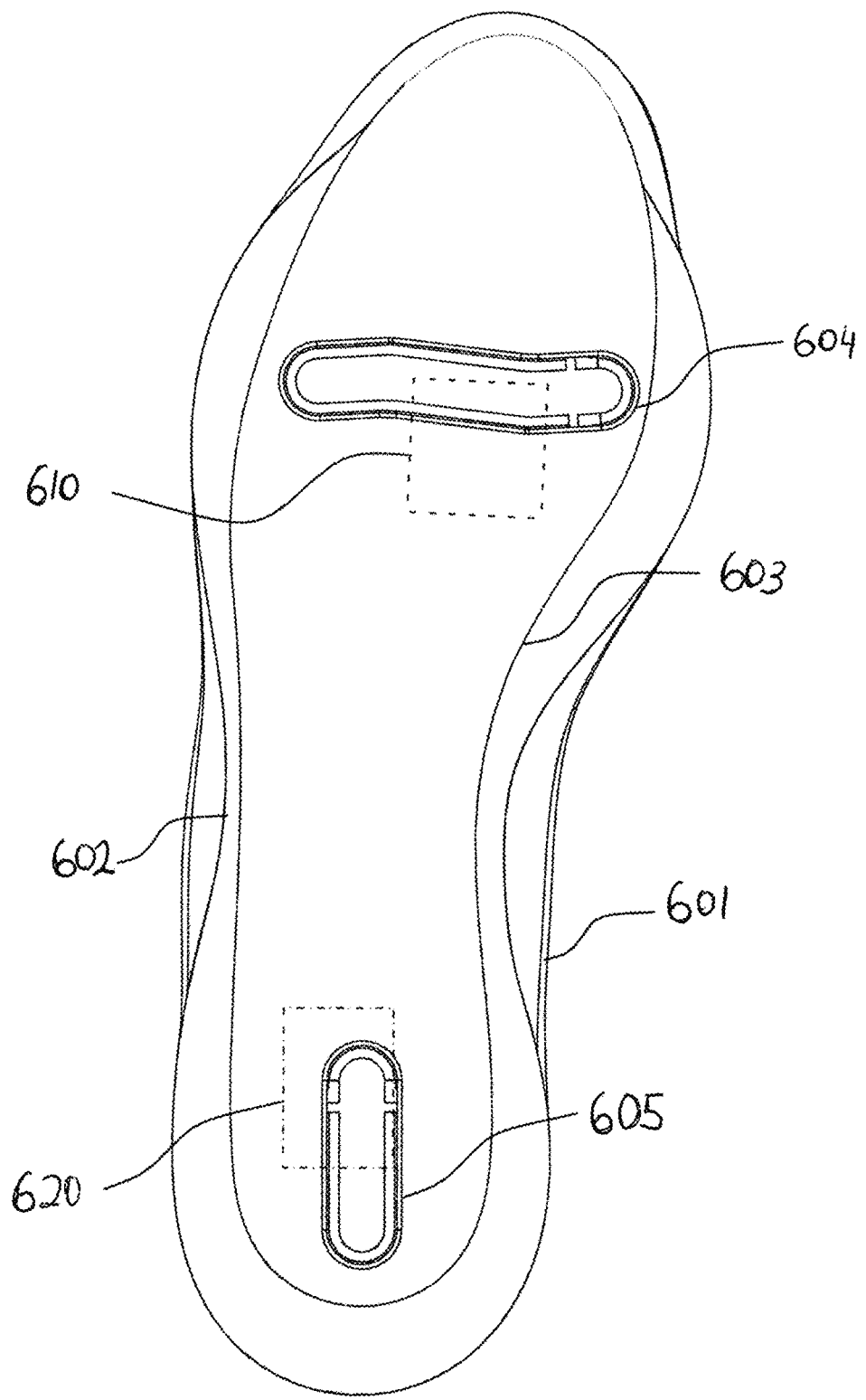
FIG. 12 illustrates effective area boundaries of positioning of the anterior and posterior protuberances with respect to a support surface, according to an embodiment.

FIG. 12 illustrates the effective area boundaries of positioning of the anterior and posterior protuberances with respect to a support surface, according to embodiments which may include treatment and alleviating pain for the following diseases and/or conditions: Medial Compartment knee OA, medial meniscus-tear/damage, Genu varus, Patello-femoral pain syndrome, Patello-femoral problem (malalignment), Lateral collateral ligamental (damage/tear), Bone bruise MTP/MFC (AVN), hip OA, Hip labrum damage (TCM), Trochanteric bursitis, Pes Anseninus bursitis, Ankle instability (supination+ext rut), Achilles tendonitis, Metatrsalgia, or a combination thereof. Indicated are the midsole 601 and outsole 602, last 603 of the foothold which may be determined by the last used in the making of the sneaker. Front rail 604 and rear rail 605 may be used for anchoring the protuberance. Indicated is the area bordered by dotted line 610 which may mark the effective area within which the peak surface of the anterior protuberance, i.e. the ground engaging surface of the anterior protuberance, may be located, while treating or alleviating pain for the diseases and/or conditions described for FIG. 12 hereinabove. Indicated is the area bordered by dotted line 620 which may mark the effective area within which the peak surface of the posterior protuberance, i.e. the ground engaging surface of the posterior protuberance, may be located, while treating or alleviating pain for the diseases and/or conditions described for FIG. 12 hereinabove. The areas bordered by dotted lines 610 and 620 may be within the areas bordered by dotted lines 504 and 505, respectively, in FIG. 10. As provided before, FIG. 10 may be divided to 36 equal parts. The effective locations may be within these effective parts regardless of sizing.

Figure 13A:
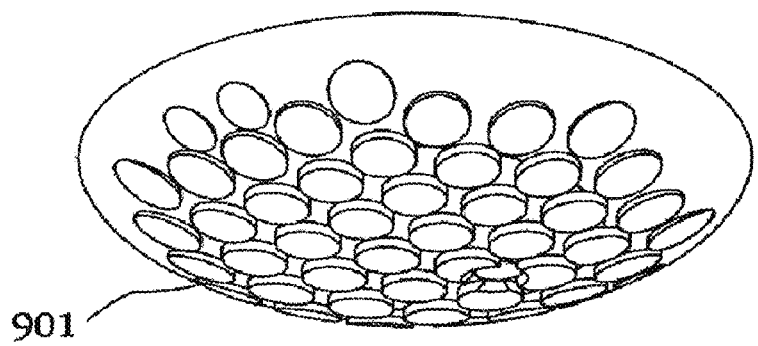
FIG. 13A is an isometric view of a protuberance suitable for use on a footwear, according to some embodiments.
Figure 13B:
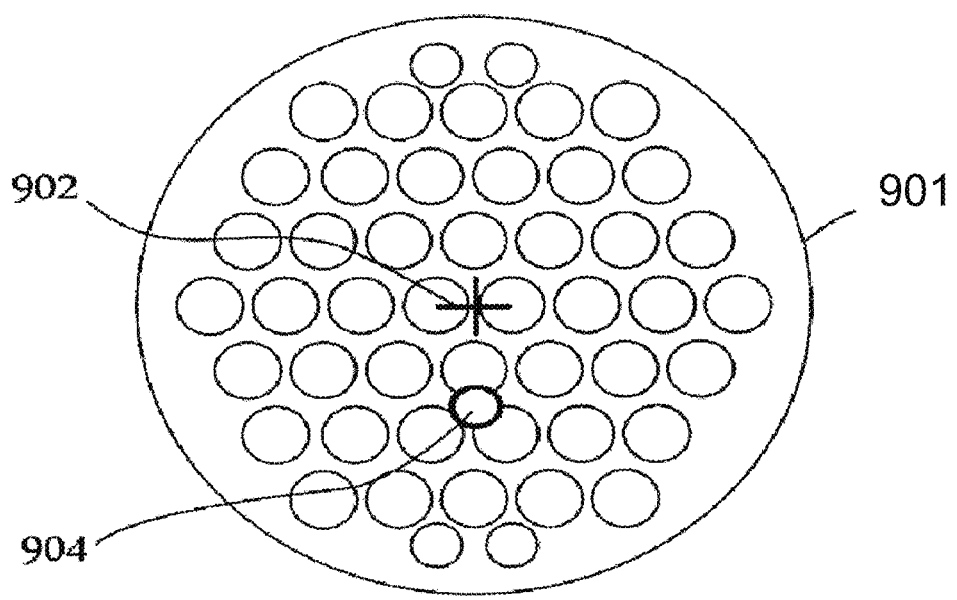
FIG. 13B is a frontal view of a protuberance suitable for use on a footwear, according to some embodiments.
Figure 13C:
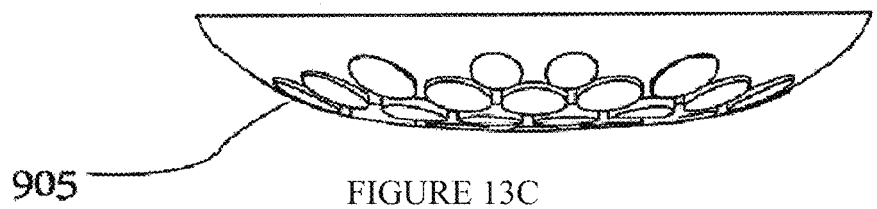
FIG. 13C is a side view of a protuberance suitable for use on a footwear, according to some embodiments.
Figure 14:
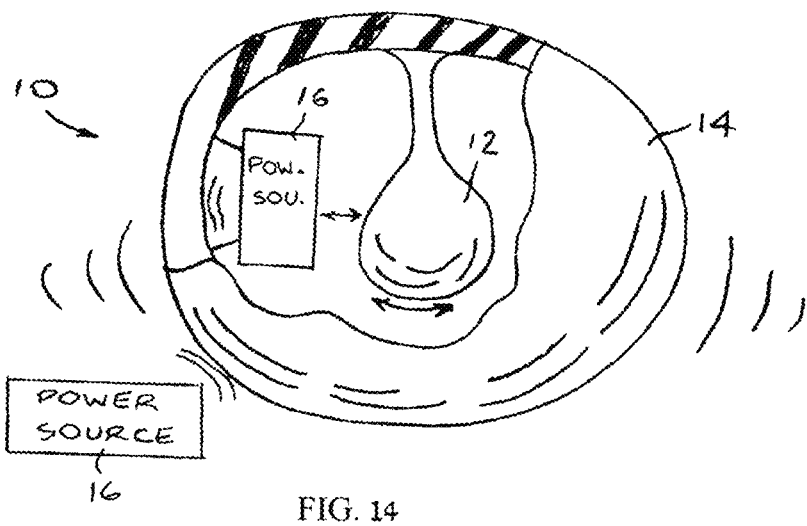
FIG. 14 is a simplified pictorial illustration of a hand-held vibrating means, constructed and operative in accordance with an embodiment.
Figure 15:
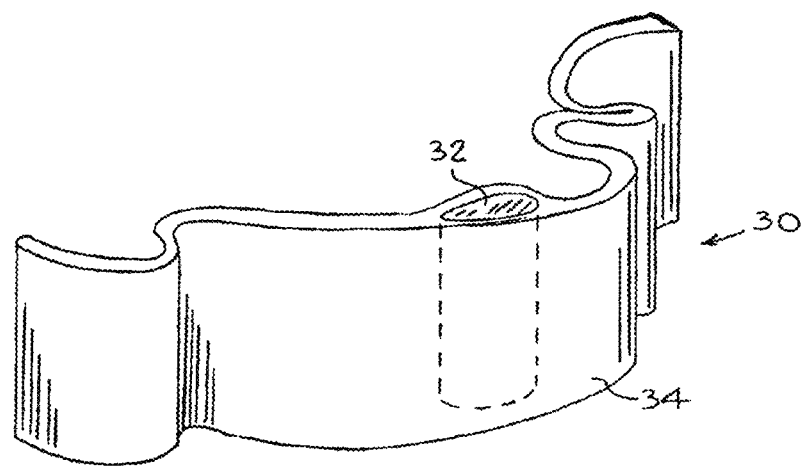
FIG. 15 is a simplified pictorial illustration of a vibrating means in the form of a wrapping, constructed and operative in accordance with another embodiment.
Figure 16:
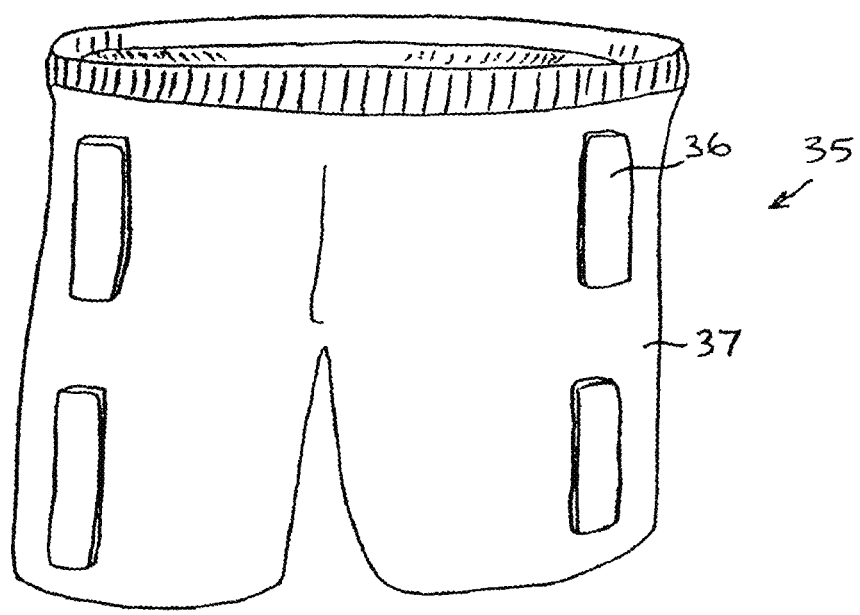
FIG. 16 is a simplified pictorial illustration of a vibrating means in the form of pants, constructed and operative in accordance with another embodiment.
Figure 17:
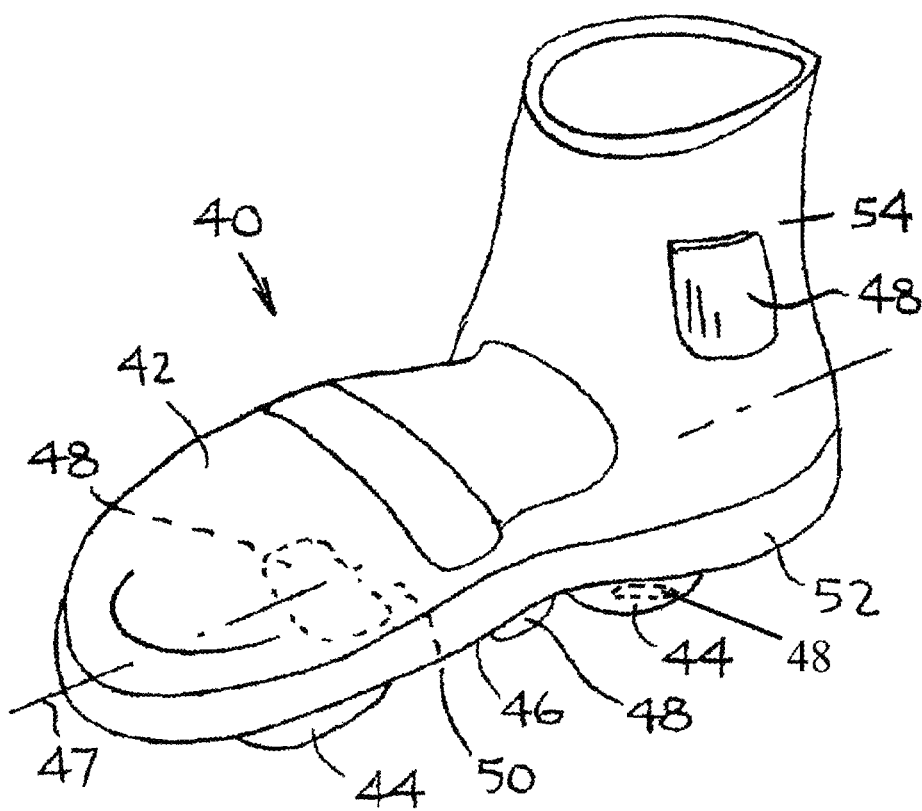
FIG. 17 is a simplified pictorial illustration of a bone-growth stimulator for footwear, constructed and operative in accordance with another embodiment.

FIG. 13A is an isometric view of a protuberance suitable for use on a footwear, according to embodiments of the present invention. Cleats 901, according to embodiments of the present invention, may cover the ground engaging area of a protuberance, for facilitating enhanced grip of the surface on which the user stands or walks. FIG. 13B is a frontal view of a protuberance suitable for use on a footwear, according to embodiments of the present invention. The peak surface may be marked by cross 902. Bore 904 may be provided for a screw or other fastening arrangement to fix the protuberance in the desired position. FIG. 18C is a side view of a protuberance suitable for use on a footwear, according to some embodiments. Convexity 905 of the protuberance is clearly seen. Various convexities may be employed, all of which may define a peak surface, typically (but not necessarily) at the center of the protuberance, which may be the surface which comes in contact with the ground, when the user attaches the support member to the foot, and walks or stands on the ground.

As described hereinabove, footwear may comprise a vibrating protuberance. As described hereinabove, footwear may comprise vibrating means located in base, cap, outsole, insole or any combination thereof. In some embodiments, vibrating means are described in U.S. Pat. No. 7,462,158 which is hereby incorporated by reference in its entirety. In some embodiments, features and uses of a device and/or footwear as described herein are described in U.S. Pat. Nos. 9,271,895, 8,533,980, 6,979,287, 7,101,330, 8,758,207, 9,357,812, 9,055,788 all of which are incorporated by reference in their entireties.

Adjustable Footwear Device and Protuberance Assembly and Methods for Such

Figure 18:
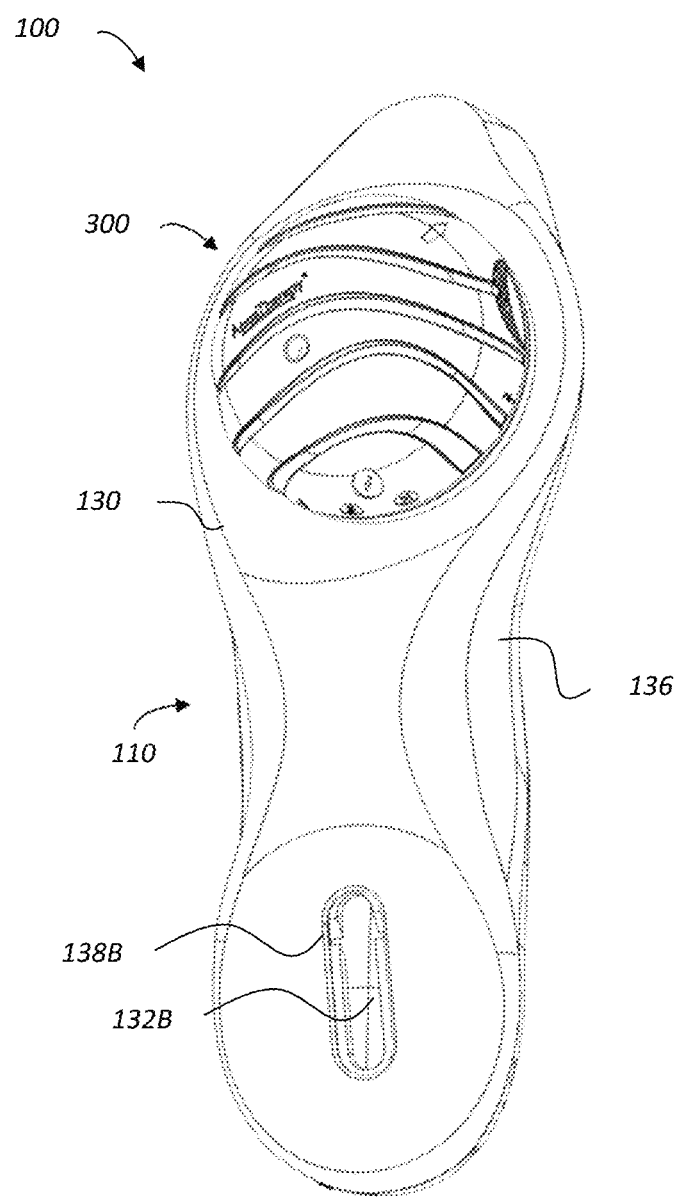
FIG. 18 shows an illustration of a perspective view of an exemplary footwear device, in accordance with an embodiment.
Figure 19:
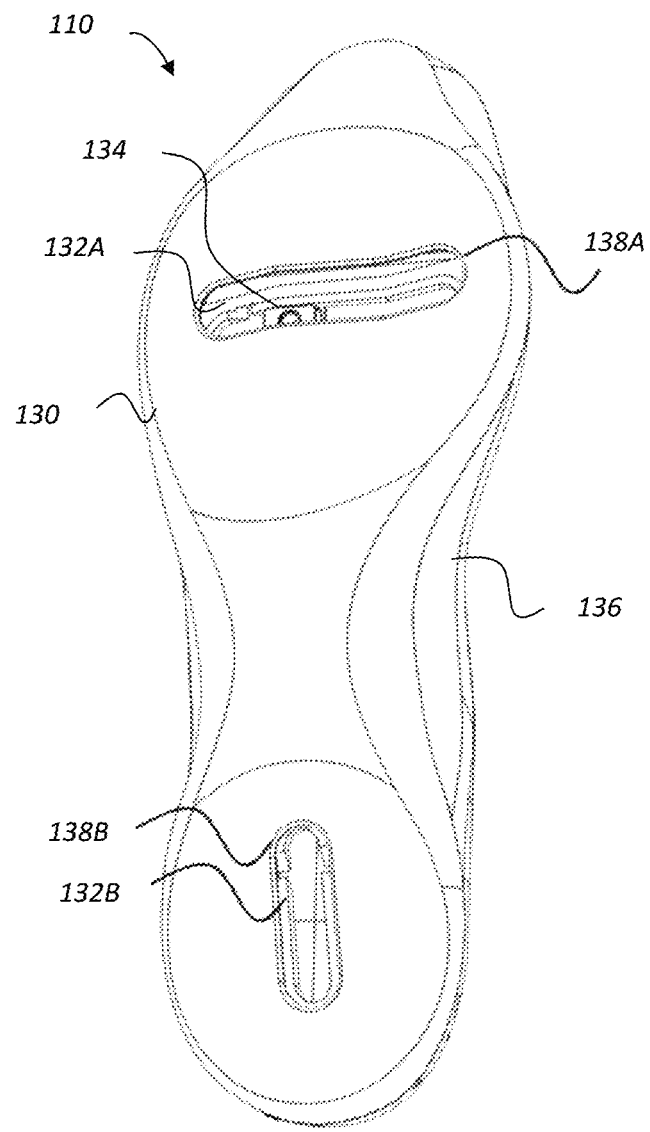
FIG. 19 shows an illustration of a perspective view of a sole assembly of the exemplary footwear device of FIG. 1.
Figure 20:
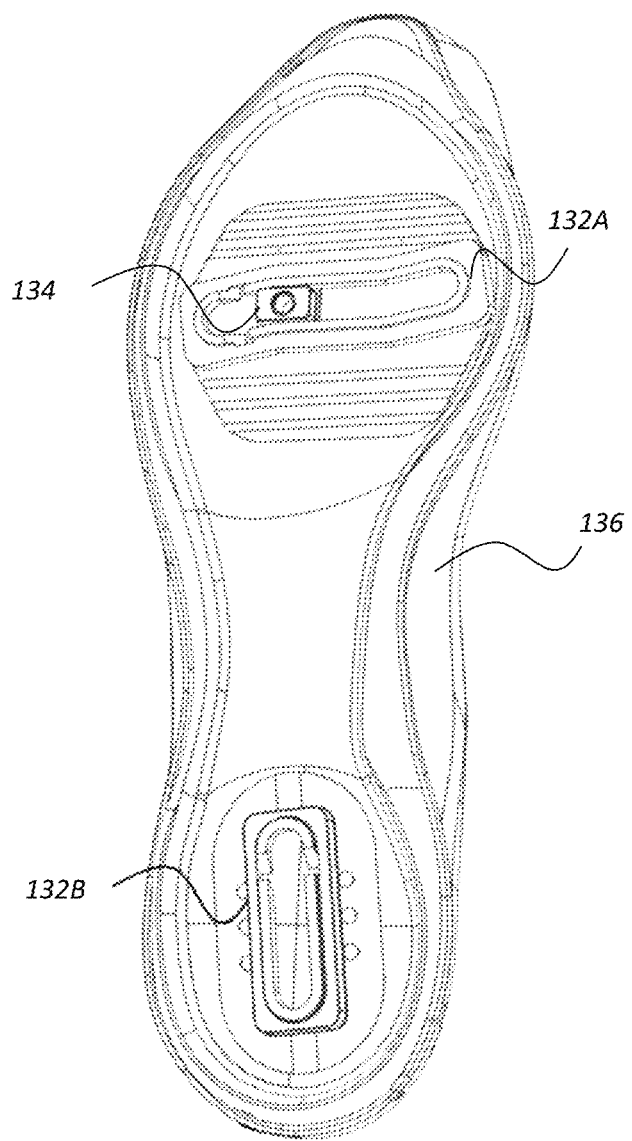
FIG. 20 shows an illustration of a perspective view of a midsole and tracks of the sole assembly of FIG. 19.

Reference is now made to FIGS. 18-20. FIG. 18 shows an illustration of a perspective view of an exemplary footwear device 100, in accordance with an embodiment. FIG. 19 shows an illustration of a perspective view of a sole assembly of exemplary footwear device 100 of FIG. 1. FIG. 20 shows an illustration of a perspective view of a midsole and tracks of the sole assembly of FIG. 19.

Device 100 may include a sole assembly 110 and a protuberance assembly 300. In some embodiments, device 100 may include multiple protuberance assembly 300 and/or more than one sole assembly 110. For example, device 100 may be a pair of shoes, where each shoe may incorporate a sole assembly configured to be attached to a pair of protuberance assemblies, e.g., one anterior and one posterior. Protuberance assembly 300 may include a base and a cap (not shown). Protuberance assembly 300 may protrude outwardly with respect to with respect to sole assembly 110. Protuberance assembly 300 may have a circular perimeter but other shapes may be also utilized. Protuberance assembly 300 may be substantially bulbous. The cap of Protuberance assembly 300 may be substantially convex. In some embodiments the cap may have a peak portion.

Device 100 may further include a locking fixture and a fastening fixture (not shown in FIGS. 18-20). Device 100 may be configured to be attached to a bottom surface of footwear item such as shoes and/or may be configured to be attached directly to a person's foot and/or may be integrated in such footwear item. Device 100 may be similar to other devices disclosed herein, such as device 10 of FIG. 1, and/or may be operated or used according to the methods disclosed herein with the required modifications.

Sole assembly 110 may include an outsole 130 and at least one track which may be an anterior track 132A and/or a posterior track 132B. Optionally, sole assembly 110 may further include a midsole 136 and/or an insole (not shown). In some embodiments, sole assembly 110 may include one or more additional sole layers. Sole assembly 110 may include additional one or more tracks. Outsole 130 may be configured to engage the ground; alternatively, outsole 130 may not be so configured, since the height of the protuberances prevents the outsole from engaging the ground. The insole may be disposed above midsole 136, on the opposite side of outsole 130. Anterior track 132A and/or posterior track 132B may be attached to midsole 136. Anterior track 132A may be disposed in an anterior portion of midsole 136. Posterior track 132B may be disposed in a posterior portion of midsole 136. The terms anterior and posterior are with respect to anterior and posterior portions, correspondingly, of a foot to which device 100 may be coupled.

Outsole 130 may include an anterior slit 138A and a posterior slit 139B. Anterior slit 138A and posterior slit 138B may be disposed in outsole 130 such that anterior track 132A and posterior track 132B are exposed towards a bottom surface of sole assembly 110 and accessible through anterior slit 138A and posterior slit 139B, correspondingly. The insole may include one or more corresponding slits.

Each of anterior track 132A and posterior track 132B may be configured to allow the positioning of protuberance assembly 300 along it (i.e. calibration of device 100). Thus, anterior track 132A and posterior track 132B may be of various shapes, lengths and/or orientations with respect to sole assembly 110 to allow various positions of protuberance assembly 300 on the bottom surface of sole assembly 110. The various positioning options of a protuberance such as protuberance assembly 300 and the effect of the position of such protuberances on a person using the disclosed footwear devices, such as device 100, may be as disclosed herein above. For example, as shown in FIGS. 18-20, posterior track 132A is horizontally oriented with respect to the bottom surface (or outsole 130) of sole assembly 110. Anterior track 132B is vertically oriented with respect to the bottom surface (or outsole 130) of sole assembly 110.

The fastening fixture may include at least one track nut 134 (or simply "nut 134") and at least one screw 330 (shown in FIG. 21), corresponding to track nut 134. Track nut 134 may be movably disposed in a track of sole assembly 110 such as anterior track 132A or posterior track 132B. For example, in FIG. 20, nut 134 is movably disposed along posterior track 132A. Screw 330 may be configured to be screwed in nut 134. The fastening fixture may be configured to fasten the base to a track, such as anterior track 132A or posterior track 132B in a selected position in the track. In some embodiments other fastening fixtures may be used in order to fasten the base to such track, as known in the art. One example is a snap mechanism, in which the track includes a socket and the base includes a pin which forcefully enters the socket and becomes secured in it.

In some embodiments, sole assembly 110 may be included in a footwear, such as a shoe. In some embodiments, sole assembly 110 may further include a securing fixture configured to secure sole assembly 110 to the footwear or to a person's foot.

Figure 21:
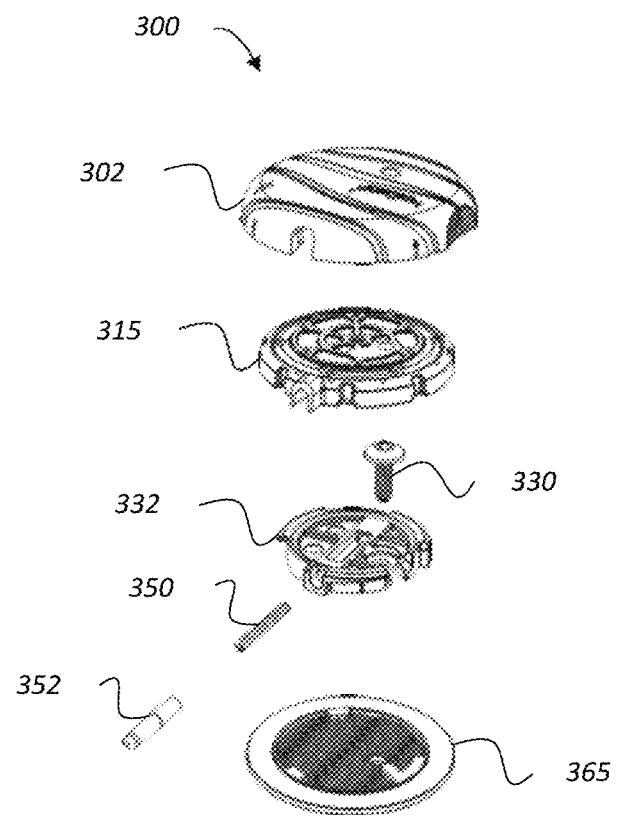
FIG. 21 shows an illustration of an exploded perspective view of a protuberance assembly of the exemplary footwear device of FIG. 18.

Reference is now made to FIG. 21 which shows an illustration of an exploded perspective view of a protuberance assembly of exemplary footwear device 100 of FIG. 18. FIG. 21 shows an illustration of another exploded perspective view of the protuberance assembly of exemplary footwear device 100 of FIG. 18.

The cap of protuberance assembly 300 may include a cap cover element 302 and a cap pivot element 315. Cap cover element 302 and cap pivot element 315 may be integrally formed, manufactured in an overmolding technique, in which cap cover element is made of a softer polymer than cap pivot element. Other techniques may be possible. The base of protuberance assembly 300 may include a base pivot element 332. The base may further include a plate insert 355

(shown only in FIG. 23, since it resides mostly inside base pivot element 332) made of a stronger material than base pivot element 332, such as metal. Plate insert 355 may reinforce base pivot element 332, serving as its inner, strong, frame. The base may further include a spacer 365 and optionally, one or more additional spacers may be used in series, to achieve a desired height. The locking fixture may include a spring 350 and a locking pin 352. The base and cap may be configured to rotatively align. The locking fixture may be configured to lock and unlock the alignment of the base and the cap. The cap and the base may be configured to rotatively align, i.e., by rotating the cap over the base.

In some embodiments, base pivot element 332 may be integrally formed with a shoe, whereas cap cover element 302 and cap pivot element 315 may be provided separately.

Figure 22:
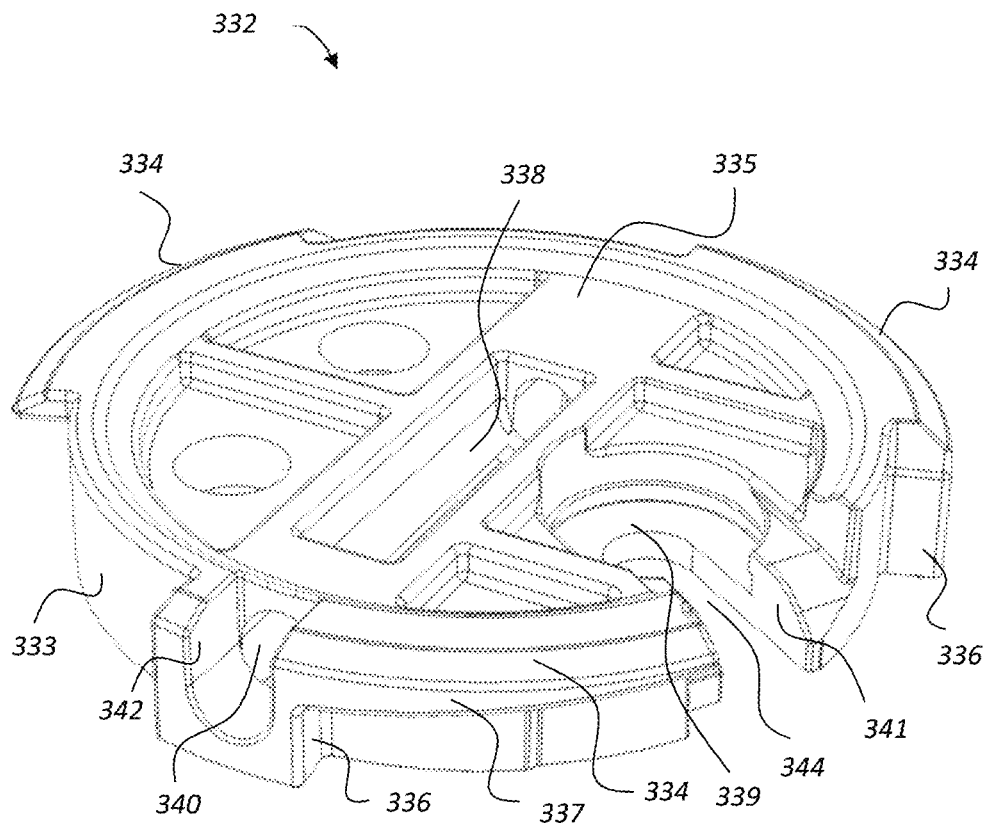
FIG. 22 shows an illustration of a perspective view of a base pivot element of a base of the protuberance assembly of FIG. 21.

Reference is now made to FIG. 22, which shows an illustration of a perspective view of base pivot element 332 of a base of protuberance assembly 300 of FIG. 21. Base pivot element 332 may have a substantially circular perimeter. Base pivot element 332 may include multiple peripheral rim portions 334, each ending with a stopper 336, a screw bore 344, a socket 338 ending with an opening 340 and a first locking channel 342. Base pivot element 332 may further include a block portion 335 and a bore level 339.

In the specific embodiment shown in FIG. 22, base pivot element 332 includes three peripheral rim portions 334. Each peripheral rim portion 334 may protrude in a centrifugal manner with respect to an external peripheral wall 333 of base pivot element 332. Each peripheral rim portion 334 may be spaced apart and thus intermittently encircle base pivot element 332. Each peripheral rim portion 334 may end with stopper 336 which may protrude downwards with respect to protuberance assembly 300. Stoppers 336 may be positioned in the ends of peripheral rim portions 334, which are in a predefined rotating direction of base pivot element 332. The predefined rotating direction may determine the rotation direction of the cap, which is required in order to align the base and the cap (i.e., the predefined rotating direction may be to the right or to the left with respect to a user rotating the cap). Stoppers 336 may protrude downwards and up to a bottom surface of base pivot element 332 (not shown). Each of peripheral rim portions 334 may further include a peripheral end portion 337 which protrudes downwards with respect to base pivot element 332 in a graduated manner. The upper surface of each peripheral rim portion 334 may be curved in order to conveniently guide the user when mounting the cap over the base.

Screw bore 344 may be partially open, to allow extracting the screw which resides therein manually even when the base and cap are connected, and may be partially encircled by a level 339. The delimiter of screw bore 344 may be in the shape of a horseshoe. Level 339 may be also shaped like a horseshoe. Screw bore 344 may be configured to allow screwing of the base to sole assembly 110. A body of screw 330 may be inserted through bore 344 and such that at least a peripheral portion of a head of screw 330 is placed against level 339. Level 339 may end with a protruding portion 341, at each side of it, configured to place the head of screw 330 on level 339 in a fixed manner. Thus, when screw 330 is screwed to sole assembly 110, it may be secured against base pivot element 332, thus attaching the base to sole assembly 110. Screw bore 344 may be positioned in an eccentric manner with respect to protuberance assembly 300.

The position of screw bore 344 may form a rotation axis, around which protuberance assembly 300 may be rotated when it is attached to sole assembly 110 (i.e., by screwing screw 330 in nut 134). Thus, multiple additional options to position protuberance assembly 300 with respect to the bottom surface of sole assembly 110 may be added per each position of protuberance assembly 300 in the track of sole assembly 110. All in all, the combination of the track and the eccentric position of screw bore 344 may allow numerous options for positioning protuberance assembly 300 with respect to the bottom surface of sole assembly 110 may be allowed.

Socket 338 may be partially open. Socket 338 may end with block portion 335 at one end and with opening 340 at its other end. Opening 340 may be at a peripheral wall of base pivot element 332. Block portion 335 may block an end portion of socket 339 from above with respect to protuberance assembly 300. In some embodiments, block portion may block a substantial portion of all of socket 338 from above. Socket 338 may be configured to accommodate the locking fixture. The locking fixture may be configured to lock the alignment of the base and the cap when it is placed in socket 338. Spring 350 may be placed in socket 338 such that at least an end portion of spring 350 is placed under block portion 335. Block portion may prevent spring 350 from leaving socket 338 when a force is applied to it.

Opening 340 may lead to first locking channel 342 (i.e., first locking channel 342 may be aligned with opening 340 and socket 338). Locking pin 352 may be positioned in socket 338 consecutively to spring 350 and such that at least an end portion of locking pin 352 is placed in first locking channel 342 and such that at least a tip portion of the end portion of locking pin 352 protrudes outwardly from locking channel 342 with respect to base pivot element 332.

In some embodiments, base pivot element 332 may include plurality of jags on its bottom surface (not shown).

The diameter of base pivot element 332, including peripheral rim portions 334 may be in the range of 40-200 millimeter (mm).

Figure 23:
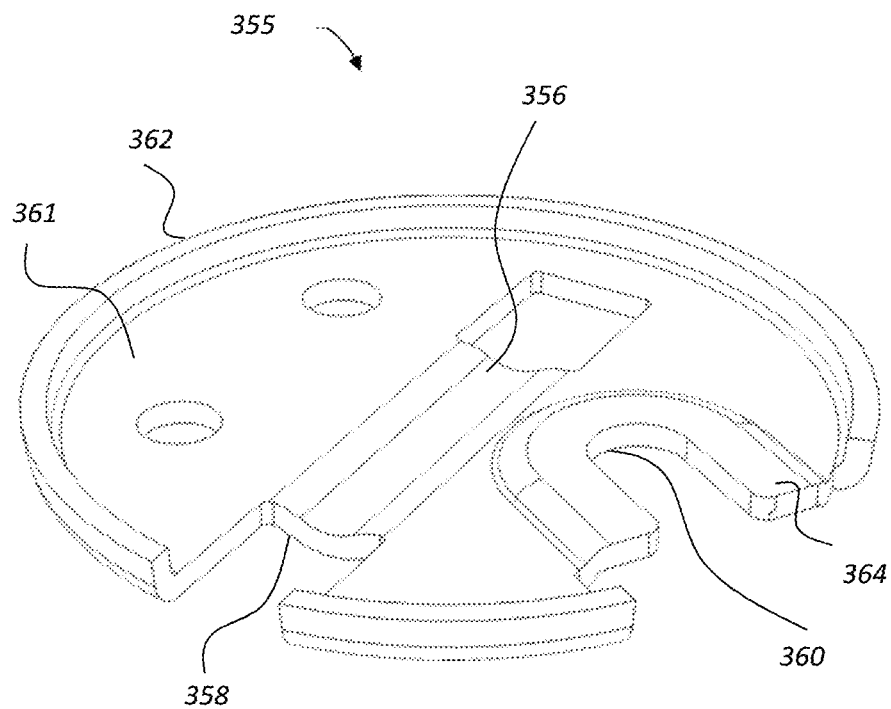
FIG. 23 shows an illustration of a plate insert of the base of the protuberance assembly of FIG. 21.

Reference is now made to FIG. 23, which shows an illustration of plate insert 355 of the base of protuberance assembly 300 of FIG. 21. Plate insert 355 may be rigid and may be made, for example, from metal. Plate insert 355 may be circular. Plate insert 355 may include a rim 362 and a screw bore 360. Plate insert 355 may further include a socket base 356, a recess 358 and/or a curved level 364. Socket base 356 may have the form of the bottom surface of socket 358 of base pivot element 332 and it may be concave with respect to a bottom surface 361 of plate insert 355. Screw bore 360 may be similar and may correspond to screw bore 344 of base pivot element 332. In some embodiments, screw bore 360 may be wider than screw bore 344. Screw bore 360 may be configured to allow the passage of the body of screw 330. Curved level 364 may circumscribe screw bore 360. Curved level 364 be curved and may protrude upwardly with respect to protuberance assembly 300. Rim 362 may circumscribe plate insert 355 and may be elevated with respect to bottom surface 361.

Figure 24A:
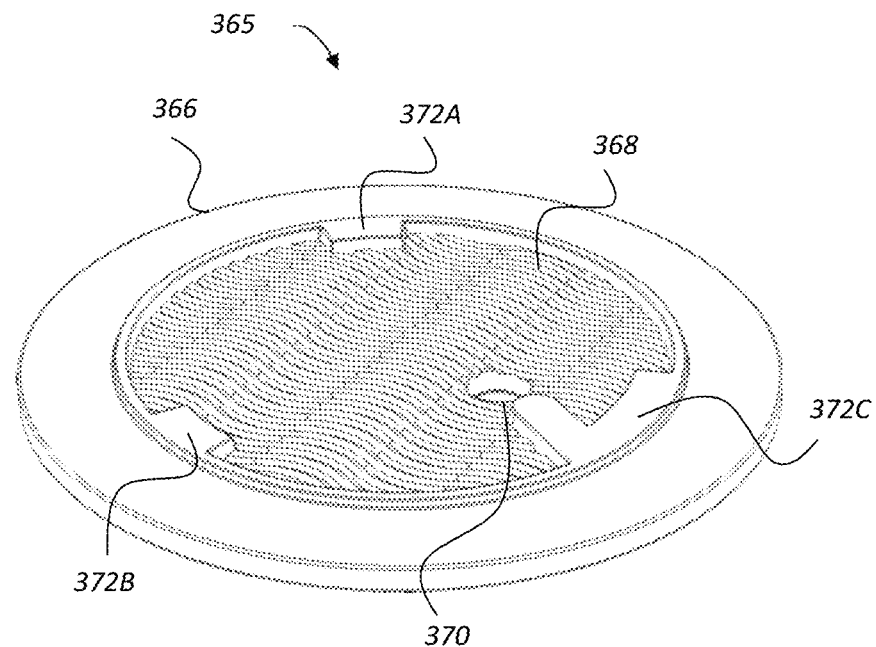
FIG. 24A shows a first spacer of the base of the protuberance assembly of FIG. 21.

Reference is now made to FIG. 24A, which shows a first spacer 365 of the base of protuberance assembly 300 of FIG. 21. First spacer 365 may be used for height adjustment of protuberance assembly 300 of FIG. 21. Multiple such spacers may be used, where different spacers may optionally have different heights and/or different elasticities. First spacer 365 may include a rim 366, an inner portion 368 and a screw bore 370. First spacer 365 may further include a first and a second holder 372A and 372B and a screw bore holder 372C. Rim 366 may circumscribe inner portion 368. Inner portion 368 may be sunk with respect to rim 366. Screw bore 370 may be configured to allow the passage of the body of screw 330.

First spacer 365 may include additional one or more holders such as first holder 372A and second holder 372B. Screw bore holder 372C may have a base portion and a protruding portion, which protrudes inwardly with respect to protuberance assembly 300. The diameter of first spacer 365 may be in the range of 40-200 mm.

Figure 24B:
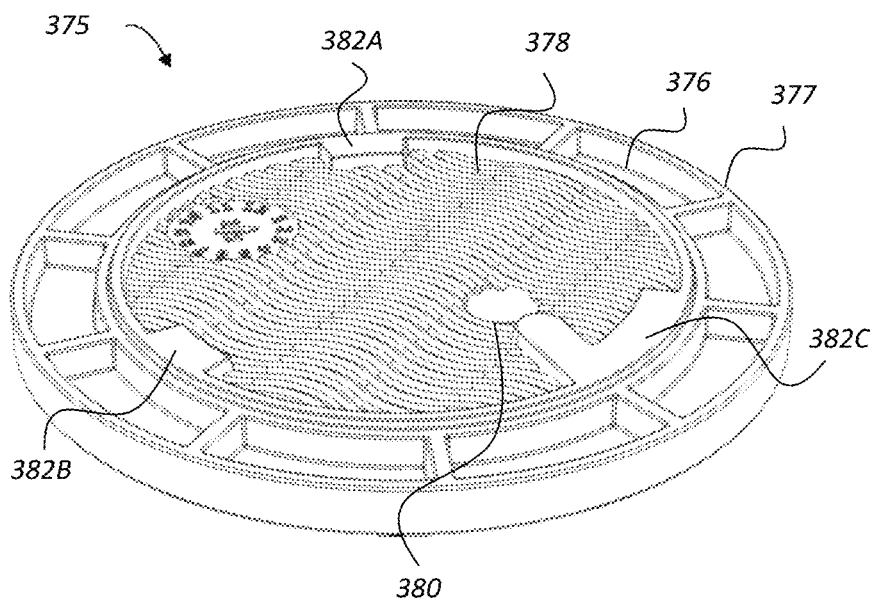
FIG. 24B shows a second spacer of the base of the protuberance assembly of FIG. 21.

Reference is now made to FIG. 24B, which shows a second spacer 375 of the base of protuberance assembly 300 of FIG. 21. This is an example of a spacer which is somewhat different than first spacer 365 of FIG. 24A. Second spacer 375 may include a dented rim 377, a wavy inner portion 378 and a screw bore 380. Second spacer 375 may further include a first and a second holder 382A and 382B and a screw bore holder 382C. Dented rim 377 may circumscribe wavy inner surface 378. Wavy inner surface 378 may be sunk with respect to dented rim 377. Wavy inner surface 368 may have a wavy and grooved top surface. Screw bore 380 may be configured to allow the passage of the body of screw 330. Dented rim 377 may include a plurality of dents 375, extending along the perimeter of rim 377. Dents 376 may be spaced apart.

First spacer 365 may correspond to second spacer 375. First spacer 365 may be positioned on second spacer 375. Wavy inner portion 368 of first spacer 365 may protrude downwardly with respect to rim 388 and first holder 372A, second holder 372B and screw bore holder 372C. Thus, the protruding bottom portion of wavy inner portion 368 of first spacer 365 may correspond to the sunken wavy inner portion 378, allowing first holder 382A, second holder 382B and screw bore holder 382C to hold such placement of first spacer 365 and second spacer 375 and substantially reduce or prevent any horizontal relative movement. In some embodiments, the bottom surface of wavy inner portion 368 of first spacer 365 may include jags which may correspond to the wavy grooved top surface of wavy inner portion 378. Thus, further fixating the placement of first spacer 365 on second spacer 375 (i.e., substantially reducing or preventing their relative movement).

Figure 25A:
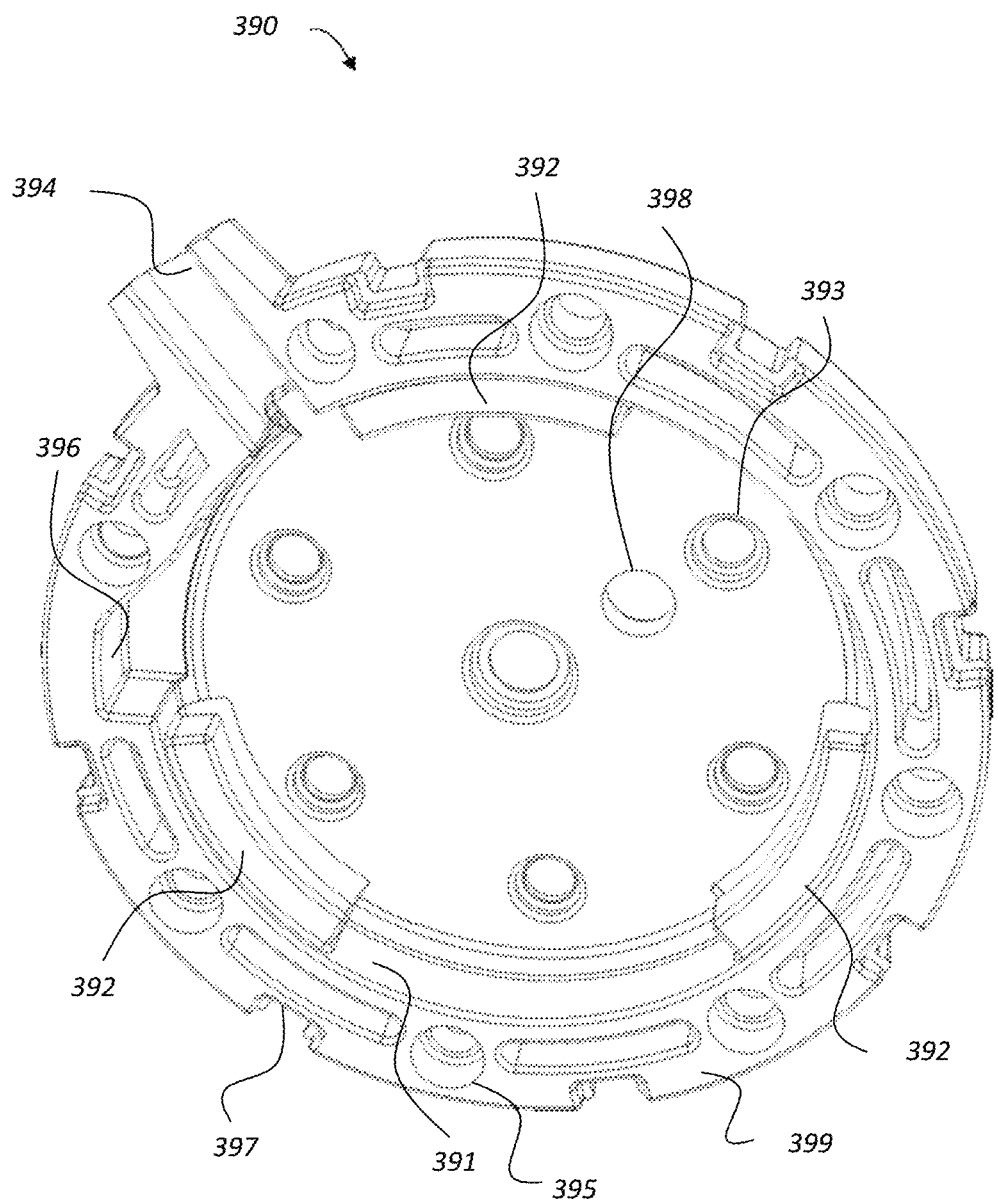
FIG. 25A shows an illustration of a perspective view of a cap pivot element of a cap of the protuberance assembly of FIG. 21.

Reference is now made to FIG. 25A, which shows an illustration of a perspective view of cap pivot element 390 of a cap of protuberance assembly 300 of FIG. 21. Cap pivot element 390 may include a plurality of internally protruding portions 392, a bore 398, a graduated recess 396 and a second locking channel 394. Cap pivot element 390 may further include a rim portion 399. The rim portion 399 may protrude downwardly with respect to the inner portion of cap pivot element 390.

Cap pivot element 390 may further include a plurality of first holding bores 393, a plurality of second holding bores 395 and/or a plurality of niches 397. In some embodiments, cap pivot element 390 may further include a plurality of protruding elements on its top surface (not shown). The plurality of first holding bores 395 may be arranged in a circular manner in the inner portion of cap pivot element 390. Second holding bores 395 may be arranged in a circular manner in rim portion 399. The protruding elements may be arranged in a circular manner on the top surface. Niches 397 may be peripherally positioned in rim portion 399. First holding bores 393, second holding bores 395, niches 397 and the protruding elements may be configured to allow a fixed attachment of cap pivot element 390 to cap cover element 302.

Cap pivot element 390 may be substantially circular. In the exemplary cap pivot element 390 shown in FIG. 25A, there are three internally protruding portions 392. However, in some embodiments, there may be less or more of such. Internally protruding portions 392 may be elongated and may be substantially rectangular. However, internally protruding portions 392 may be of other shapes. Internally protruding portions 392 may be disposed along an internal peripheral wall 391 of cap pivot element 390 and may be spaced apart. Each of internally protruding portions 392 may correspond to one of peripheral rim portions 334 of base pivot element 332. Bore 398 may be positioned correspondingly to screw bore 344 of base pivot element 332. Bore 398 may be configured to allow access to screw 330, when it is screwed through screw bore 344 in nut 134 of sole assembly 110 (e.g., in order to further screw said screw bore 344), through the cap. Graduated recess 396 is a graduated recess in in internal peripheral wall 391, which may be positioned adjacent to second locking channel 394 and prior to it in the predefined rotating direction. Second locking channel 394 may extend from an opening in the internal peripheral wall 391 outwardly with respect to protuberance assembly 300. Second locking channel 394 may correspond to first locking channel 342 of base pivot element 332.

When the cap is placed on the base and rotated in the predefined rotating direction, each of the internally protruding portions 392 may arrive under its corresponding peripheral rim portion 334 and stopped by the downward protruding stopper 336 of each of the peripheral rim portion 334, correspondingly, thereby aligning the base and the cap. The second locking channel 394 may be then aligned with the first locking channel 342 and such that the second locking channel 394 may be positioned outwardly to the first locking channel 342 and in a consecutive manner.

When the cap is placed on the base, the protruding tip portion of locking pin 352 may fit in the most recessed portion of graduated recess 396. Thus, when the cap is rotated in the predefined rotating direction, the graduated wall of graduated recess 396 may gradually push locking pin 352 and thereby compress spring 350, such that the tip portion of locking pin 352 is inserted into first locking channel 342. Thus, the rotation of the cap over the base may be allowed. When second locking channel 394 is aligned with first locking channel 342, the tip portion of locking pin 352 may be pushed outwardly into second locking channel 394 by compressed spring 350. As a result, the rotation of the cap over the base is stopped (i.e., blocked by the tip portion of locking pin 352 confined by second locking channel 394) and the cap and the base are now fixedly aligned.

In order to unlock the alignment of the cap and the base, an elongated element may be used to push locking pin 352 back into first locking channel 342. The cap may be then at least slightly rotated against the predefined rotating direction and such that internally protruding portions 392 may be released from under peripheral rim portions 334 of base pivot element 332. The cap, and specifically, first cap pivot element 390, may be then removed from the base and base pivot element 332, specifically.

Figure 25B:
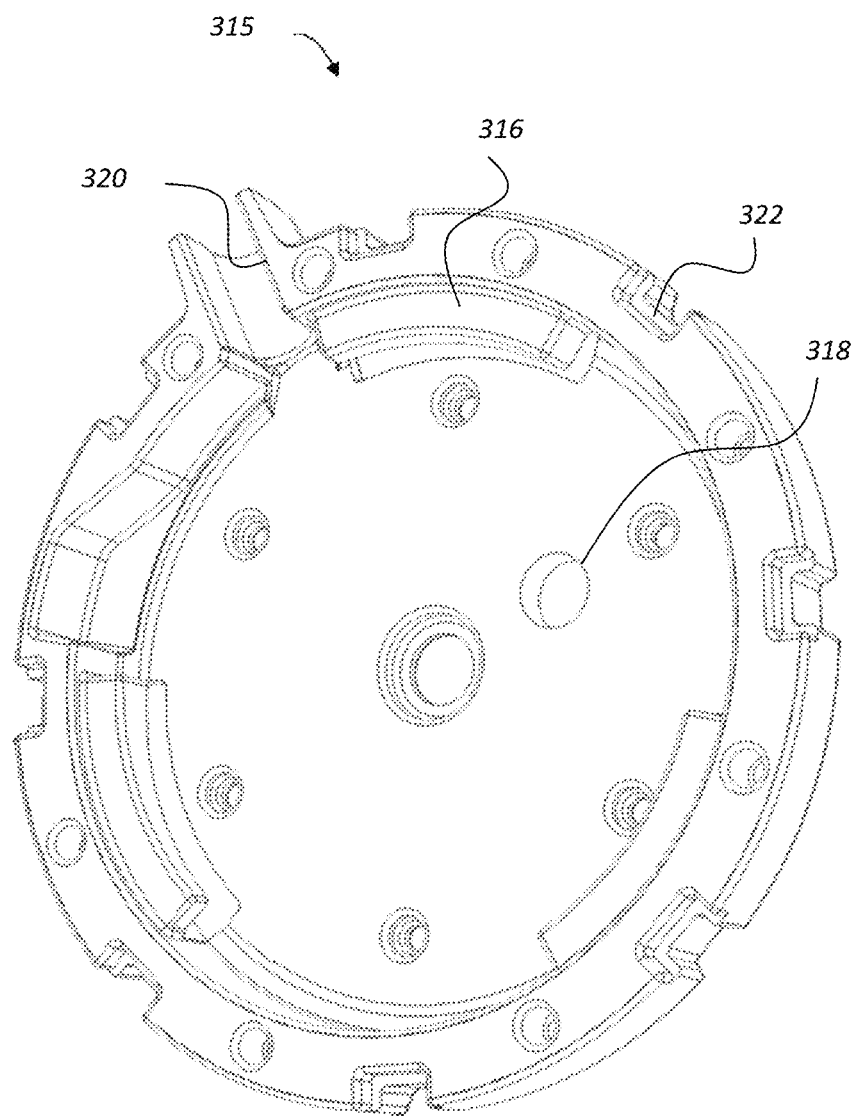
FIG. 25B shows an illustration of a perspective view of another cap pivot element of a cap of the protuberance assembly of FIG. 21.

Reference is now made to FIG. 25B shows an illustration of a perspective view of cap pivot element 315 of a cap of protuberance assembly 300 of FIG. 21.

Figure 26:
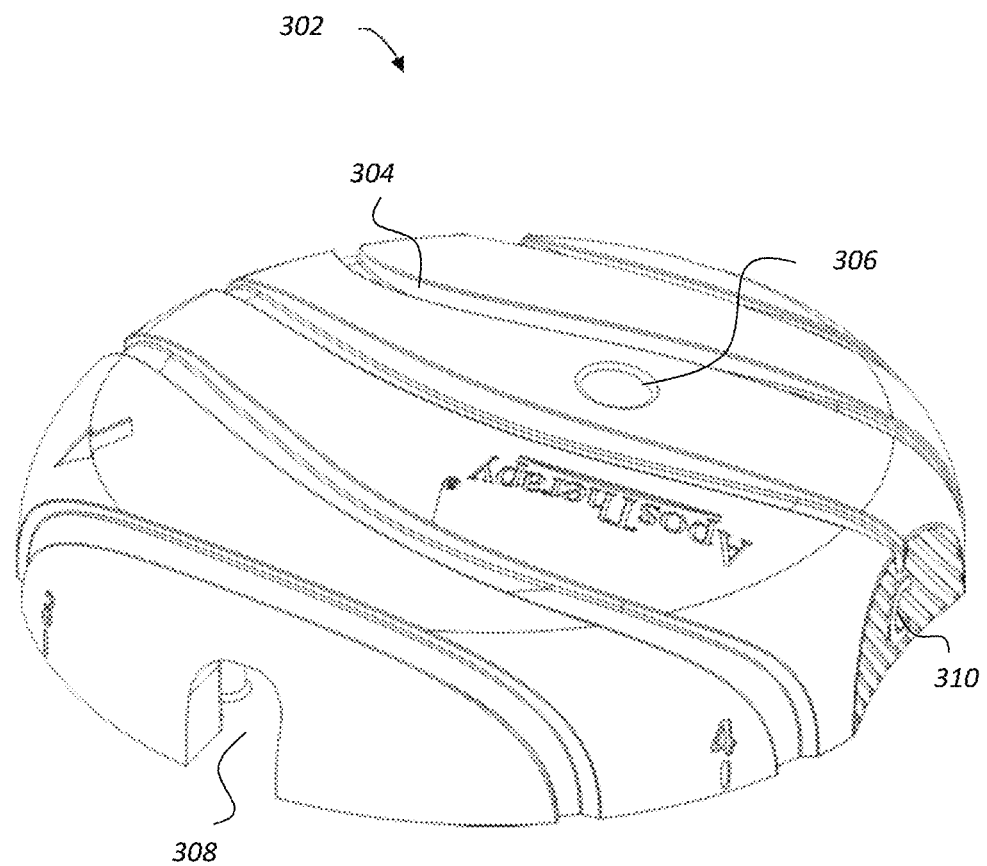
FIG. 26 shows an illustration of a cap cover element of the cap of the protuberance assembly of FIG. 21.

Reference is now made to FIG. 26, which shows an illustration of a cap cover element 302 of the cap of protuberance assembly 300 of FIG. 21. Cap cover element 302 may be configured to cover cap pivot element 390. Cap cover element 302 may be peripherally circular. Cap cover element 302 may include a bore 306 and an opening 308. Cap cover element 302 may further include grooves 304 and/or a grip surface 310. Bore 306 may correspond to bore 398 of cap pivot element 390. Bore 306 may be configured to allow access to screw 330, when screwed in nut 134 of the fastening fixture. Opening 308 may be configured to allow access to locking pin 352 (i.e., in order to unlock the alignment of the base and the cap) and may accordingly correspond to the second locking channel 394 of cap pivot element 390. Cap cover element 302 may be configured to engage the ground. Accordingly, grooves 304 may form friction when engaging the ground, to allow a more stable interaction between a patient using device 100 and the ground. Grip surface 310 may be positioned peripherally on the external surface of cap cover element 302. Grip surface 310 may form a truncated portion in cap cover element 302 and may be coarse, thus facilitating user's grip of the cap.

Cap cover element 302 may further include a plurality of protruding elements (not shown), protruding from its bottom surface, which may come in contact with the top surface of cap pivot element 390, when assembled or attached together to form the cap. The plurality of protruding elements may correspond to the plurality of first holding bores 393, second holding bores 395 and/or niches 397. The protruding elements may be disposed in first holding bores 393, second holding bores 395 and/or niches 397 such that the attachment of cap cover element 302 and cap pivot element 390 is firmly held.

The diameter of cap cover element 302 may be in the range of 40-200 mm.

Device 100 may be operated and used in accordance with the method of FIG. 27, as described herein below.

Figure 27:
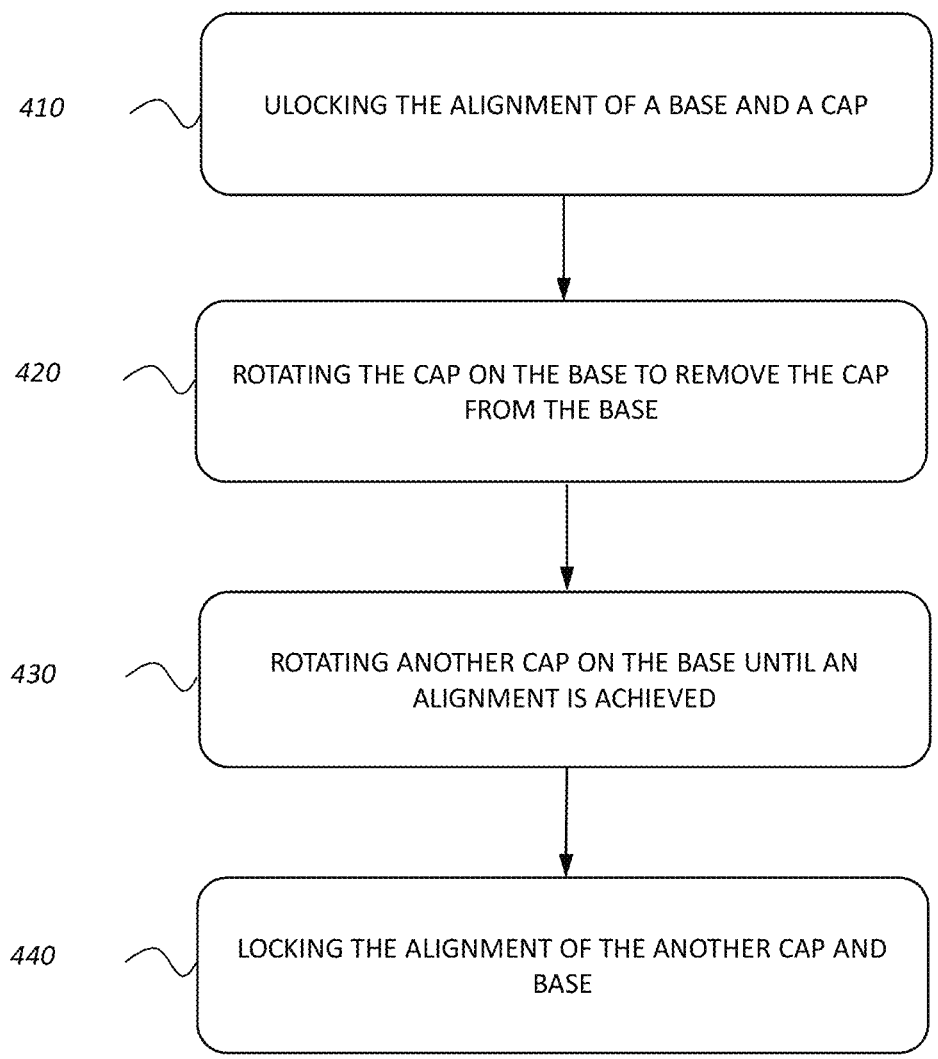
FIG. 27 shows a flow chart of a method for adjusting a footwear device in accordance with an embodiment.

Reference is now made to FIG. 27, which shows a flow chart of a method for adjusting a footwear device, such as device 100, in accordance with an embodiment. The footwear device may include a protuberance assembly, such as protuberance assembly, mounted to a selected position in a bottom surface of a sole, such as sole assembly 110. The protuberance assembly may include a base and a cap, where the base and cap may be aligned and locked. The cap and the base may be rotatively aligned. In a step 410, the alignment of the base and cap may be unlocked. The unlocking may be performed by releasing a locking fixture of the footwear device, which may lock the alignment of the base and cap. For example, the locking fixture may be similar to the locking fixture of device 100 and may be released as described herein above with respect to device 100.

In a step 420, the cap may be rotated on the base to remove the cap from the base. The base may be kept firmly mounted to the selected position in the bottom surface of the sole. A reference is now made to FIG. 28, which shows a base of protuberance assembly 300 of FIG. 4 mounted on a bottom surface of sole assembly 110 of FIG. 19. The base may be firmly mounted to sole assembly 110 by screw 330, screwed in nut 134 (not shown in the Figure) of the fastening fixture. Nut 134 may be placed in a track of sole assembly 110, such as posterior track 132A (as shown in FIGS. 19 and 20).

Figure 28:
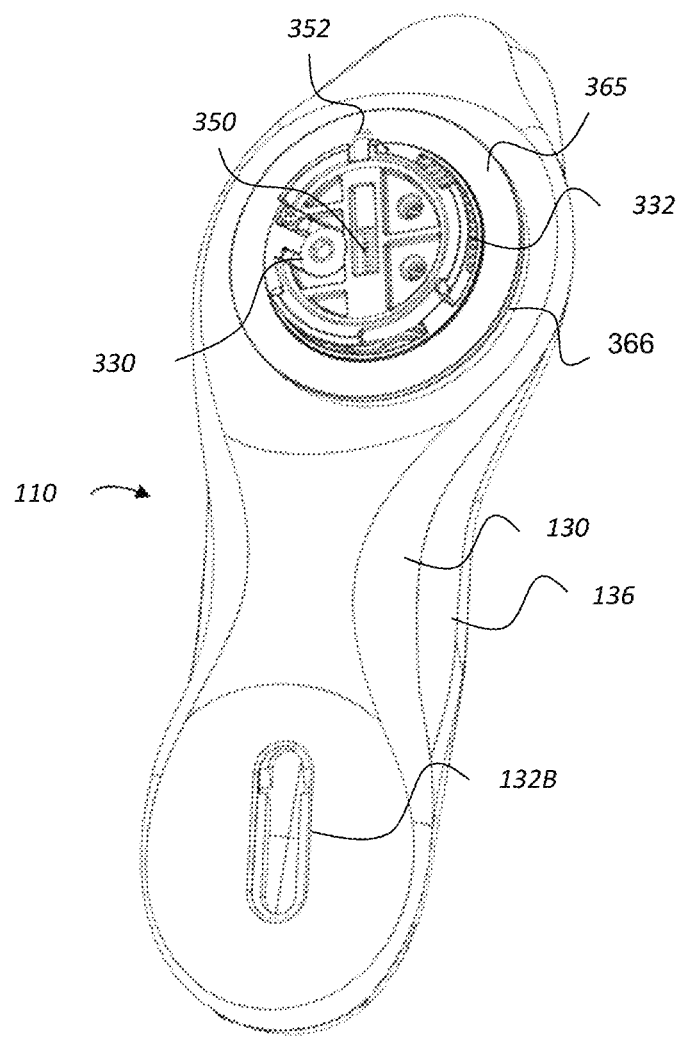
FIG. 28 shows a base of the protuberance assembly of FIG. 4 mounted on a bottom surface of the sole assembly of FIG. 19.

In a step 430, another cap may be rotated on the base until an alignment of the another cap with the base is achieved. With reference to FIG. 28, another may be now rotated on the base. The alignment may be achieved as described herein above with respect to device 100. In some embodiments, the another cap may be similar to the removed cap. In such cases the removed cup may be replaced, for example due to wear or damage caused to the removed cap. In some embodiments, the another cap may be different from the removed in at least one characteristic of the cap, which may affect the patient using the device. Such characteristic may be. For example, the size, the height or a curvature measure of the cap. Such replacement of the removed cap may be required, for example, due to a change in a treatment plan of a user or when moving to a different phase of the treatment plan.

In a step 440, the alignment of the another cap and the base may be locked. The locking of the alignment may be performed by a locking fixture. The locking fixture may be, for example, the locking fixture of device 100 which may be locked as described herein above with respect to device 100.

In an optional step, the device may be calibrated by firmly mounting the protuberance assembly to the selected position in the bottom surface of said sole. With reference to FIG. 28, the base may be firmly mounted to the selected position by screwing screw 330. The calibration process may be performed as described herein above with respect to the various disclosed methods and devices. The calibration may be performed when initially mounting a protuberance assembly to a sole or a sole assembly, or whenever is required.

It should be noted that, as an alternative to the track(s) discussed throughout the above specification and shown in FIGS. 1-28, a sole may include a different connective element (not shown) which facilitates a connection to a base and/or a protuberance. For example, connection may be facilitated by a screw and socket mechanism, where the socket is in the sole and the screw is in or is threaded through the base/protuberance, or vice versa. In one embodiment, a "connective element" comprises a screw and a socket. In one embodiment, a "connective element" comprises a bolt. In one embodiment, a "connective element" comprises a nail, peg, spike, track, brad, or any combination thereof. The socket may be provided with a nut matching the threads of the screw. It is explicitly intended that wherever a track is referred to above, such element be interpreted to also cover the option of the different connective element, as discussed in this paragraph.

EXAMPLES

In all case studies pain is presented as graded by the patient on a 10 cm Visual analogue scale. The ends of the scale were defined as 0—no pain and 10—worst pain imaginable. A pain of 4/10 means 4 cm out of 10 cm.

After each change in the systems calibration (footwear or device of the invention) the patient is asked to walk a distance of 10 meters away from the therapist and then back in order to verify that the patient remains balanced and that the change in calibration created the desired positive effect (i.e. reduction in pain, improvement of timing of the heel-strike, improved control of knee motion etc').

In the prescription (treatment plan), patients are instructed to wear the system on daily basis for a certain amount of time (in a typical treatment plan the patient is initially required to wear the system for 30-60 minutes a day). It is important to emphasize that this does not mean walking with the system, rather it is the overall treatment time and the patient is instructed to spend this time performing basic day to day activities of indoors daily living such as watching TV, computer time. Thus, patients typically spend 10-20% of the day in weight bearing activities. This ensures a gradual process of getting accustomed to walking with the system whilst maintaining the functionality of the treatment. In this manner any adverse effects, such as muscle cramps and muscle pain, can be avoided.

Gait is being measured in a gait lab meaning spatio-temporal measurements that are tested by various computerized mats as well as three-dimensional gait labs or any other known method for measuring velocity, step length and single limb support. Unless noted otherwise, gait lab is done when patient is barefoot.

Physiological values of Single Limb Support are between 38%-40% of the step cycle. In some pathologies (e.g. medial compartment knee osteoarthritis, medial meniscal tear etc') the single limb support is usually lower than 40% and sometimes lower than 38%. In other pathologies (e.g. hypermobility of the joints) single limb support is usually higher than 40%.

In the "pain" section of the calibrations a repeated shift is described in order to bring the patient to a reduced pain calibration. In the cases a shift of 2 mm is repeated between 1-3 times until reaching the desired effect. However, we wish to clarify that the process can more than 3 times and shift can be 1 cm eventually from the "balanced" position and even more until the desired effect is achieved. As long as the shift does not result in excessive eversion or inversion.

Example 1: Non-Union of a Mid-Shaft Fracture of the Left Tibia

A 38 years old male patient presented to the treatment center due to a non-union of a mid-shaft fracture of the left tibia. The patient was injured 1 year prior to the initial consultation in a motor cycle accident. The fracture was treated by an open reduction and an internal fixation (ORIF) with an intra-medullary nail. Due to the non-union he had undergone a second surgery 3 months after the initial ORIF which included a bone graft and a replacement of the ORIF. The patient reported pain in all weight bearing activities in and around the area of the fracture (VAS 2-3/10). The pain worsened after standing for more than 10 minutes (VAS 4/10) and walking for more than 50 meters (VAS 5/10).

Physical Examination

On observation the patient was standing with decreased weight bearing on the left leg. Ranges of motion of the knees and ankle were within normal limits. Clinical gait assessment revealed a decreased stance period on the left and a mild circumduction of the left during the swing phase.

Imaging and Gait Lab

An X ray performed a month before the consultation showed mild signs of a formation of a callus around the fracture, but an X ray performed 5 months prior revealed the same amount of classification. Gait lab results (see table 1) showed velocity of 87 cm/sec, single limb support (measured in % of gait cycle) of 34.7% in the left leg and 39.1% in the right leg. Step length: Left: 54 cm Right: 57 cm.

Therapy

BP's: Identical BP's with a C convexity and hard resilience were attached and fixed to the patients system under the hind foot of the right and left systems. In order to induce bone growth a vibrating unit was attached and fixed between the posterior BP of the patients left system. In order to maintain an even leg length, 4 hard 2 mm spacers were attached and fixed between the sole of the right system and the right posterior. In order to avoid a plantar flexed position of both ankle 4 hard 2 mm spacers were inserted and fixed between the sole of the both systems and the anterior BP's.

Balancing Process: The patients system was calibrated and fine tuned during repeated clinical gait assessments. During this process care is taken to reduce the eversion and inversion during heel strike, loading response, mid-stance and toe-off.

Pain: In order to reduce pain in tibia, the posterior left BP was calibrated 1-2 mm to a more anterior position and fixed in the new location. Patient was then asked to walk 20 meters with the system and reported reduction of pain from 3/10 to 0/10.

Heel-Rise Timing: Patient was asked to walk 20 m in order to confirm that he is still balanced and the heel-rise is well timed in the gait cycle. It was noted that the patient had well timed heel rise in both legs.

Vibrating unit (vibrating means): the vibrating unit was then activated at a frequency of 30 Hz and the patient was asked to walk again. There were no visible gait deviations and the patient reported he felt comfortable during ambulation.

Prescription/Treatment Plan: The patient was now briefed with safety instructions and guided how to turn the vibrating unit on and off. He was instructed to turn the unit on before wearing the system and to turn it off once he has finished using it. The patient was asked to wear the system at home for 45 minutes a day on each day of the first week of the treatment. Out of this total wearing time he was instructed to spend an accumulative time of 13-15 minutes in weight bearing activities (walking or standing while performing daily routine-see item 3 in the clarification section). The patient was instructed to increase overall daily wearing time of the system by 15 minutes every week for the initial 4 weeks, reaching an hour and 45 minutes of total wearing time with the system every day (reaching an accumulative weight bearing time of approximately 25-30 minutes). The patient was seen for follow up consultations and assessments at the Treatment center 4 weeks after his first visit, 3 months after his first visit and 5 months after his first visit. Each follow up consultation consisted of a Gaitlab test, an interview performed by the treating AposTherapist (including report of current symptom level rated on a VAS and report of difficulty in function), a clinical assessment of gait without and with the system as well as changes in the calibration of the system and a treatment plan for the duration of time till the next follow up.

Treatment Progression: As was described above the patient immediately reported a reduction in pain while walking with the Apos system during the initial consultation. In the first follow up consultation he reported the pain level in tibia was reduced to maximum pain level of 1/10. He found walking and standing easier (difficulty level less than 1/10). He has been wearing the system according to the treatment plan indoors performing daily activities (accumulative weight bearing time with the system of 30 minutes). Clinical gait assessment revealed a reduction in the circumduction of the left leg. Computerized barefoot gait assessment showed improvement in gait velocity, bilateral step length and left single support (see table 1 for details). Gait assessment with the system did not reveal any deviations and the patient reported he felt comfortable walking with it. He was instructed to increase the indoors of the system by 15 minutes a week to a maximum of 4 hours.

The second follow up consultation was performed 3 months after the initial consultation. The patient then reported he had no pain during weight bearing activities. An X-ray taken a week before the consultation showed the formation of callus around the fracture has increased so that about 40% of the width of the fractures tibia was fused. A barefoot gaitlab test revealed an increase in gait velocity to 90.2 cm/sec. Step length has increased to 55.3 cm in the left leg and 57.5 cm in the right leg. Single limb support was increased to 35.3.1% in the left leg and decreased 38.7% in the right leg (see table 1). These values indicate that the patient had a more symmetrical gait since the difference between step length and single limb support of the right and left legs has decreased. A clinical gait assessment with the system did not reveal any deviations and the convexity level of all BP's was increased to C with a soft resilience. The patient was instructed to maintain his current activity level with the system.

In the third follow up, which was carried out 5 months after the beginning of the treatment, the patient has reported his pain has completely abated and he could walk or stand as much as his daily activities demanded. An X ray taken 10 days prior to the consultation has shown a full callus has been formed fusing the tibia completely. A barefoot gaitlab test revealed an increase in gait velocity to 12.0 cm/sec. Step length in the left leg was 63.1 cm and 64.3 cm in the right leg. Single limb support 37.8% in the left leg and 38.5% in the right leg indicating better gait symmetry (see table 1). The patient was than instructed to stop using the vibration unit and the system. Following this initial phase treatment, the patient was seen regularly for follow up consultations twice a year at the treatment center.

TABLE 1

Patient's gait parameters

| Visit | Velocity (cm/sec) | Left step length (cm) | Right Step length (cm) | Left Single Limb Support (in % of step cycle) | Right Single Limb Support (in % of step cycle) |
| --- | --- | --- | --- | --- | --- |
| $1^{st}$ (initial) | 87 | 54 | 57 | 34.7 | 39.1 |
| $2^{nd}$ (first follow-up) | 90.2 | 54.3 | 57.5 | 35.3 | 38.1 |
| $3^{rd}$ (second follow-up) | 120..1 | 63.1 | 64.3 | 37.8 | 38.5 |

Example 2: Osteoporosis Tibia

A 70 years old female patient presented to the treatment center with osteoporosis.

Case History: The patient was 20 years post menopause. The patient was hardly engaged in physical activity. The patient has been diagnosed with osteoporosis 3 years prior to the consultation. She has been treated with 30 mg of alendronic acid (Fosalan) once a week for the past two and a half years with no improvement in bone mass.

Physical Examination: The patients BMI was 19.9. On observation there were no obvious malalignments of the lower limbs or spine. Ranges of motion of the spine, hips, knees and ankles were within normal limits. Clinical gait assessment did reveal any gait deviations.

Imaging and Gait lab: Bone mass (BMD) density: the BMD tests results indicated a current state of −3.1 T in the femoral neck and −2.7 T at the L 2 vertebra. Gait lab results (see table 2) showed velocity of 110 cm/sec, single limb support (measured in % of gait cycle) of 38.9% in the left leg and 39.1% in the right leg. Step length: Left: 26 cm Right: 56.3 cm.

Therapy

BP's: Identical BP's with B convexity and hard resilience were attached and fixed to the patients system under the hind foot of the right and left systems. In order to induce bone growth a vibrating unit was attached and fixed between the posterior BP's of the patients systems. In order to avoid a plantar flexed position of both ankle 4 hard 2 mm spacers were inserted and fixed between the sole of the both systems and the anterior BP's.

Balancing Process: The patients system was calibrated and fine-tuned during repeated clinical gait assessments. During this process care is taken to reduce the eversion and inversion during heel strike, loading response, mid-stance and toe-off.

Pain: Since the patient did not complain of any pain this stage of the process was not performed.

Heel-Rise Timing: Patient was asked to walk 20 m in order to confirm that she is still balanced and the heel-rise is well timed in the gait cycle. It was noted that the patient had normal timing of heel rise in both legs.

Vibrating unit: the vibrating unit was then activated at a frequency of 35 Hz and the patient was asked to walk again. There were no visible gait deviations and the patient reported she felt comfortable during ambulation.

Prescription/Treatment Plan: The patient was now briefed with safety instructions and guided how to turn the vibrating unit on and off. She was instructed to turn the unit on before wearing the system and to turn it off once she takes the system off. The patient was asked to wear the system at home for an hour a day on each day of the first week of the treatment. Out of this total wearing time she was instructed to spend an accumulative time of 15-20 minutes in weight bearing activities (walking or standing while performing daily routine-see item 3 in the clarification section). The patient was instructed to increase overall daily wearing time of the system by 15 minutes every week for the initial 4 weeks, reaching a total of two hours with the system every day (reaching an accumulative weight bearing time of approximately 30-35 minutes). The patient was seen for follow up consultations and assessments at the treatment center 4 weeks after her first visit, 4 months after her first visit and 7 months after her first visit. Each follow up consultation consisted of a Gaitlab test, an interview performed by the treating Therapist, a clinical assessment of gait without and with the system as well as changes in the calibration of the system and a treatment plan for the duration of time till the next follow up.

Treatment Progression: In the first follow up consultation the patient reported she felt comfortable using the system while she was performing daily activities. She has been wearing the system according to the treatment plan and has built up the wearing time to two hours (accumulative weight bearing time with the system of 40 minutes). Computerized barefoot gait assessment showed normal values for all the parameters tested (see table 2 for details). Gait assessment with the system did not reveal any deviations and the patient reported she felt comfortable walking with it. The patient was then instructed to increase the overall wearing time of the system by 20 minutes per week up to a maximum of 5 hours.

The second follow up consultation was performed 4 months after the initial consultation. The patient reported she was using the system on a daily basis for a duration of 4-6 hours a day. She felt comfortable with it and did not report any adverse effects. A barefoot gait lab test continued to show normal values for all the parameters (see table 2). A clinical gait assessment with the system did not reveal any deviations and the convexity level of all BP's was increased to C with a hard resilience. Reassessment of the gait with the new BP's was normal and the patient reported she felt comfortable. The patient was instructed to maintain her current activity level with the system.

In the third follow up, which was carried out 7 months after the beginning of the treatment, the patient has reported she was still wearing the system for 5 hours per day. A repeated BMD scan showed that bone mass has increased to −2.0 T in the femoral neck and −1.9 T at the L 2 vertebra. Since there were no changes made in her medication or her level of activity it was believed that the treatment has led to this improvement in BMD. Gaitlab indicated normal results. Gait assessment with the system showed a normal gait pattern. The patient was asked to continue using the system at the current level.

Following that the patient was seen regularly for follow up consultations at the treatment center twice a year.

TABLE 2

Patient's gait parameters

| Visit | Velocity (cm/sec) | Left step length (cm) | Right Step length (cm) | Left Single Limb Support (in % of step cycle) | Right Single Limb Support (in % of step cycle) |
|---|---|---|---|---|---|
| 1st (initial) | 110 | 56 | 56.3 | 39.1 | 38.8 |
| 2nd (first follow-up) | 115 | 57 | 57 | 38.9 | 38.8 |
| 3rd (second follow-up) | 116 | 56 | 57 | 39.0 | 39.1 |

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for adjusting a device comprising a protuberance assembly mounted to a selected position on a bottom surface of a sole, said protuberance assembly comprising a base and a cap, wherein said base and cap are aligned and locked, the method comprising:
   unlocking the alignment of said base and cap;
   rotating said cap on said base to remove said cap from said base, wherein said base is kept firmly mounted to said selected position in said bottom surface of said sole; rotating another cap on said base until and alignment of said another cap with said
   base is achieved; and
   locking said alignment of said another cap and said base,
      wherein said sole comprises at least one track and said protuberance assembly comprises a fastening fixture which comprises:
         a track nut movably disposed in said track; and
         a screw configured to be screwed in said nut,
            wherein said base comprises a screw bore positioned in an eccentric manner with respect to said protuberance assembly, said screw bore configured to allow fastening of said base to said track in said selected position by said screw and said track nut, and
         said cap comprises a bore positioned correspondingly to said screw bore configured to allow access to said screw through said cap.

2. The method of claim 1, wherein said base further comprises a socket ending with an opening in a peripheral wall of said base, said socket configured to accommodate a locking fixture, said locking fixture comprising a locking pin and a spring, and wherein said locking fixture is configured to lock said alignment of said base and cap when placed in said socket.

3. The method of claim 1, further comprising calibrating said device by firmly mounting said protuberance assembly to said selected position in said bottom surface of said sole.

* * * * *